US006121034A

United States Patent [19]

Laroche et al.

[11] Patent Number: 6,121,034
[45] Date of Patent: Sep. 19, 2000

[54] ***CONIOTHYRIUM MINITANS* XYLANASE GENE CXY1**

[75] Inventors: André J. Laroche; Timothy Y. Huang; Michele M. Frick; Zhen-Xiang Lu; Hung Chang Huang, all of Lethbridge; Kuo Joan Cheng, Richmond, all of Canada

[73] Assignee: Her Majesty the Queen in right of Canada, as represented by the Minister of Agriculture and Agri-Food, Lethbridge, Canada

[21] Appl. No.: 09/311,170

[22] Filed: May 13, 1999

[51] Int. Cl.[7] ...................... C12N 9/42

[52] U.S. Cl. .................... 435/209; 435/69.1; 435/320.1; 435/3; 435/254.11; 435/255.5; 435/23.2; 435/252.3; 536/23.2; 536/23.1

[58] Field of Search .................... 435/209, 69.1, 435/320.1, 3, 254.11, 255.5, 252.3; 536/23.2, 23.1

[56] References Cited

U.S. PATENT DOCUMENTS

| | | | |
|---|---|---|---|
| 5,457,046 | 10/1995 | Woldlike et al. | 435/209 |
| 5,763,254 | 6/1998 | Wöldlike et al. | 435/209 |

FOREIGN PATENT DOCUMENTS

WO 99/02662 1/1999 WIPO .

OTHER PUBLICATIONS

Altschul, S.F.; Madden, T. L..; Schaeffer, A.A.; Zhang, J.; Miller, W. and Lipman, D.J. (1997) Gapped BLAST and PSI–BLAST: a new generation of protein database search programs. Nucleic Acids Res.25:3389–3402.

Arai, M.; Kawaguchi, T. and Sumitani, J. (1998) Xyalanase gene from *Aspergillus aculeatus*. Genbank accession No. AB013110, direct submission.

Blanco, J.; Coque, J.J.; Velasco, J. and Martin, J.F. (1997) Cloning, expression in *Streptomyces lividans* and biochemical characterization of a thermostable endo–beta–1,4–xylanase of *Thermomonospora alba* ULJB1 with cellulose–binding ability. Appl. Microbiol. Biotechnol. 48:208–217.

Bieley, P. (1985) Microbial xylanolytic systems. Trends Biotechnol. 3:286–290.

Brosius, J.; Erfie, M. and Storella, J. (1985) Spacing of the –10 and –35 regions in the tac promoter. J. Biol. Chem. 260:3539–3541.

Davis, G. And Henrissat, B. (1995) Structures and mechanisms of glycosyl hydrolases. Structure 3:853–859.

Ellis, S.B.; Brust, P.F.; Koutz, P.J.; Water, A.F.; Harpold, M.M. and Gingeras, R.R. (1985) Isolation of alcohol oxidase and two other methanol regulated genes from the yeast *Pichia pastoris*. Mol. Cel.. Biol. 5:1111–1121.

Fontes, C.M.G.A.; Hazelwood, G.P.; Morag, E.; Hall, J.; Hirst, B.H. and Gilbert, H.J. (1995) Evidence for a general role for non–catalytic thermostabilizing domains in xylanases from thermophillic bacteria. Biochem, J. 307:151–158.

Gerhardt, P.; Murray, R.G.E.; Wood, W.A. and Krieg, N.R. (1994) Methods for General and Molecular Bacteriology. American Society for Microbiology. Washington, D.C., USA.

Gilbert, J.J.; Sullivan, D.A.; Jenkins, G.; Kellett, L..E.; Minton, N.P., et al. (1988) Molecular cloning of multiple xylanase genes from *Pseudomonas fluorescens* subsp. cellulosa. J. Gen. Microbiol. 134:3239–3247.

Gilkes, N.R.; Henrissat, B., Kilburn, D.G.; Miller, R.C. Jr. and Warren, R.A.J. (1991) Domains in microbiol β–1, 4–glycanases: sequence conservation, function, and enzyme families. Microbiol. Rev. 55:303–315.

Greprinet, O.; Chebrou, M.–C. and Beguin, P. (1988) Purification of *Clostridum thermocellum* xylanase Z expressed in *Esherichia coli* and identification of the corresponding product in the culture medium of *Clostridium thermocellum*. J. Bacteriol. 170:4576–4581.

Haas, H.; Friedlin, E.; Stoffler, G. and Redl, B. (1993) Cloning and structural organization of a xylanase–encoding gene from *Penicillium chrysogenum*. Gene 126:237–242.

Hall, J.; Hazlewood, G.P.; Huskisson, N.S.; Durrant, A.J. and Gilbert, H.J. (1989) Conserved serine–rich sequences in xylanase and cellulase from *Pseudomonas fluorescens* subsp. cellulosa: internal signal sequence and unusual protein processing. Mol. Microbiol. 3: 1211–1219.

Henrisssat, B.; Clayssens, M.; Tomme, P.; Lemesle, L. and Mornon, J.–P. (1989) Cellulase families revealed by hydrophobic cluster analysis. Gene 81:83–95.

Henrissat, B. and Bairoch, A. (1993) New families in the classification of glycosyl hydrolases based on amino acid sequence similarities. Biochem. J. 293: 781–788.

Huang, H.C. and Hoes, J. A. (1976) Penetration and infection of *Sclerotinia sclerotiorum* by *Coniothyrium minitans*. Can. J. Bot. 54: 406–410.

Huang, H.C. and Kokko, E.G. (1987) Ultrastructure of hyperparasistism of *Coniothyrium minitans* on sclerotia of *Sclerotinia sclerotiorum*. Can. J. Bot. 65: 2483–2489.

Huang, H.C. and Kokko, E.G. (1988) Penetration of hyphae of *Sclerotinia sclerotiorum* by *Coniothyrium minitans* without the formation of appressoria. J. Phytopathology 123: 133–139.

Ito, K.; Ikemasu, T. and Ishikawa, T. (1992) Cloning and sequencing of the xynA gene encoding xylanase A of *Aspergillus kawachii*. Biosci. Biotechnol. Biochem. 56: 906–912.

(List continued on next page.)

*Primary Examiner*—Rebecca E. Prouty
*Assistant Examiner*—Richard Hutson
*Attorney, Agent, or Firm*—Greenlee, Winner and Sullivan, PC

[57] ABSTRACT

The nucleotide sequence of a novel xylanase gene obtained from the soilborne fungus *Coniothyrium minitans,* and denoted cxy1, is provided. The amino acid sequence of the encoded xylanase enzyme, denoted Cxy1, is also provided.

20 Claims, 10 Drawing Sheets

OTHER PUBLICATIONS

Iikura, H.; Takashima, S.; Nakamura, A.; Masaki, H. and Uozumi, T. (1997) Cloning of a gene encoding a putative xylanase with a cellulose–binding domain from *Humicola grisea*. Genbank accession No. AB001030, direct submission.

Jones, D.; Gordon, A.H. and Bacon, J.S.D. (1974) Cooperative action by endo– and exo–β–(1–3)–glucanases from parasitic fungi in the degradation of cell wall glucans of *Sclerotinia sclerotiorum* (Lib.) de Bary. Biochem. J. 140: 45–55.

Laemmli, U. K. (1970) Cleavage of structural proteins during the assembly of the head of bacteriophage T4. Nature 227: 680–685.

MacCabe, A.P., Fernandex–Espinar, M.T., de Graaff, L.H., Visser, J. and Ramon, D. (1996). Identification, isolation and sequence of the *Aspergillus nidulans* xlnC Gene encoding the 34–kDa xylanase. Gene 175: 29–33.

Nielsen, H.; Engelbrecht, J.; Brunak, S. and von Heijne, G. (1997) Identification of prokaryotic and eukaryotic signal peptides and prediction of their cleavage sites. Protein Engineering. 10: 1–6.

Ruiz–Roldan, M.C.; Huertas–Gonzales, M.D.; DiPietro, A. and Roncero, M.I.G. (1998) Two xylanase genes of the vascular wilt pathogen *Fusarium oxysporum* f. sp. lycopersici differentially expressed during infection of tomato plants. Genbank accession No. AF052582, direct submission.

Sambrook, J.; Fritsch, E.F. and Maniatis, T. (1989) Molecular Cloning, A Laboratory Manual. Cold Spring Harbor Laboratory Press. 7.37–7.87, 9.47–9.62, 2.108–2.125.

Sheppard, P.O.; Grant, F.J.; Oort, P.J.;, Sprecher, C.A.; Foster, D.C.; Hagen, F.S.; Upshall, A.; McKnight, G.L. and O'Hara, P.J. (1994) The use of conserved cellulase family–specific sequences to clone cellulase homologue cDNAs from *Fusarium oxysporum*. Gene 150: 163–167.

van Rooijen, G.J.H. and Moloney, M.M. (1994) Plant seed oil–bodies as carriers for foreign proteins. Bio/Technology 13:72–77.

Wood, P.J.; Erfle, J.D. and Teather, R.M. (1988) Use of complex formation between congo red and polysaccharides in detection and assay of polysaccharide hydrolases. Methods Enzymol. 160: 59–74.

Wong, S.–L. (1989) Development of an inducible and enhancible expression and secretion system in *Bacillus subtilis*. Gene 83:215–223.

i) Forward primer:

Alignment:

| aa: | E | N | S/G | M | K | W | D | A | |
|---|---|---|---|---|---|---|---|---|---|
| 1. | 5' GAG | AAC | AGC | ATG | AAG | TGG | GAT | GCC | 3' |
| 2. | GAG | AAC | AGC | ATG | AAG | TGG | GAT | | |
| 3. | GAG | AAC | AGC | ATG | AAA | TGG | GAC | GCG | |
| 4. | GAG | AAC | GGC | CAG | AAG | TGG | GAC | GCC | |

Semi-degenerate primer Ff1:

5' GAG AAT AGC ATG AAA TGG GAT GC GC 3' (SEQ ID NO: 3)
                C           G    C

Fig. 1A ii Reverse primer:

Alignment:

| aa: | T/S | V/I | W | G/Q | V/F | S/A | D |
|---|---|---|---|---|---|---|---|
| 1. 5' | ACT | GTC | TGG | GGT | GTC | TCT | GAC 3' |
| 2. | ACC | GTC | TGG | GGA | GTT | GCT | GAC |
| 3. | ACC | GTC | TGG | GGA | GTG | TCC | GAC |
| 4. | AGC | ATC | TGG | CAG | TTT | GCC | GAC |

Consensus sequence Ff5:

5'  ACT GTC TGG GGT GTG TCT GAC 3' (SEQ ID NO: 4)
            C        A   T G C
                         C A

Reverse semi-degenerate primer Fr5:

3'  TGA CAG ACC CCA CAC AGA CTG 5' (SEQ ID NO: 5)
     G            T   A C G
                      G T

Fig. 1B

```
ccgtctgcatcatctctgccatcatgcgtacctctgtcctgcccctcataatcgcccc    60
                  M  R  T  S  V  L  A  L  I  I  A  P          12 actgccgttcggtcagtcccagctttggagccagtgtggtggcaatggatggtccggg   120
 T  A  V  F  G  Q  S  Q  L  W  S  Q  C  G  G  N  G  W  S  G   32 cctacgacttgtgtttccgatcggtgtgtagcaaagtgaatgactggtacttccagtgt   180
 P  T  T  C  V  S  G  S  V  C  S  K  V  N  D  W  Y  F  Q  C   52 attcctggctcggggcggggggatctccagctcccagctcccaccaccgccgcaggaagcagccct   240
 I  P  G  S  G  G  G  G  S  P  A  P  T  T  T  A  A  G  S  S  P   72 actcccaccccaggcgcacagggcacacaggggccggaggtggtctacacgacaagttcatggccaaggc   300
 T  P  T  Q  G  T  G  A  G  G  G  L  H  D  K  F  M  A  K  G    92 aagacctactccggtactgagatcgacaactaccatctgaacaacgcccctttgctgct   360
 K  T  Y  F  G  T  E  I  D  N  Y  H  L  N  N  A  P  L  L  A   112 atcgccaaaagcagctttggtcaggtcacatgcgagaacagcatgaaatgggatgccacg   420
 I  A  K  S  S  F  G  Q  V  T  C  E  N  S  M  K  W  D  A  T   132
```

Fig. 2A

```
gaaccgcgacgtggaacattcaacttcggcaacgctgattccgtcgtcaactgggccacg    480
 E  P  R  R  G  T  F  N  F  G  N  A  D  S  V  V  N  W  A  T     152 tcgaacggaaagctcgtccgtggccacaccctcctttggcacagccagttgccgagctgg    540
 S  N  G  K  L  V  R  G  H  T  L  L  W  H  S  Q  L  P  S  W     172 gtcacccagatcagtgaccgcacaacattgacatcgtcatcgaaaaccacgtgacacag    600
 V  T  Q  I  S  D  R  T  T  L  T  S  V  I  E  N  H  V  T  Q     192 atggtcacgcattacaagggcaagattctccaatgatgtagttaatgagatcttcgcc    660
 M  V  T  H  Y  K  G  K  I  L  Q  W  D  V  V  N  E  I  F  A     212 gaggatggtaacctccgagacagcgtcttcagccgtgtgctgctccggcgaggacttcgttggc    720
 E  D  G  N  L  R  D  S  V  F  S  R  V  L  G  E  D  F  V  G     232 atcgccttccgcgctctccgcgccgatcctaacgcgaagctctacattaatgattat    780
 I  A  F  R  A  A  R  A  A  D  P  N  A  K  L  Y  I  N  D  Y     252 aacctcgacatcgcaaactatgcaaaggtgaccaaaggcatggtcgagcacgtcaacaaa    840
 N  L  D  I  A  N  Y  A  K  V  T  K  G  M  V  E  H  V  N  K     272 tggggtgtcgcagggcatcccatcgacggcatcggctcgcaggccatcttgcagcaccc    900
 W  V  S  Q  G  I  P  I  D  G  I  G  S  Q  A  H  L  A  A  P     292
```

Fig. 2B

```
ggtgggtggaactcggcgtctggcgttcccaacgcactcaagacgctggccggcgccaac   960
 G  G  W  N  S  A  S  G  V  P  N  A  L  K  T  L  A  G  A  N    312 gtcaagagatcgccgtcactgagctcgacattgtcggcgcgtcggcaaacgactacctc   1020
 V  K  E  I  A  V  T  E  L  D  I  V  G  A  S  A  N  D  Y  L    332 accgtcatgaacggctgtctcgccgtgcccaagtgcgtcggtattactgtttgggtgtc   1080
 T  V  M  N  G  C  L  A  V  P  K  C  V  G  I  T  V  W  G  V    352 tccgacaaggacagctggcgcagtagcgacagccctctgttcgacagcaactacaat    1140
 S  D  K  D  S  W  R  S  S  D  S  P  L  L  F  D  S  N  Y  N    372 gccaagcaggcgtacaccacactgctcaacgcgttgtaaaggattctggagacaatcggt   1200
 A  K  Q  A  Y  T  T  L  L  N  A  L                            384 cgtagtattaggatagattaaatcatgcttgccagcaggtaataaagcccgaaaaaaaaa  1260 aaaaaaaaa                                                      1269
```

Fig. 2C

```
Cxyl    ---MRTSVLALIIAPTAVFGQSQLWSQCGGNGWSGPTTCVSGSVCSKVNDWYFQCIPGSG    57
Xyl3    ---MHTFSVLLALAPVSALAQAPIWGQCGGNGWTGATTCASGLKCEKINDWYYQCVPGSG    57
Ffam1   ---MHTFSVLLALAPVSALAQAPIWGQCGGNGWTGATTCASGLKCEKINDWYYQCVPGSG    57
XynA    ------MVQIKAAALAMLFAS---------------------------------------    15
FIa     ------MVQIKAAALAVLFAS---------------------------------------    15
Xylnc   ------MVHLKTLAGSAVFAS---------------------------------------    15
Pxyn    ---MIPNITQLKTAALVMLFAG--------------------------------------    19
Xyla    MTETRHRPSRRARRSLSLLLTS--------------------------------------    22

Cxyl    GGSPAPTTTAAGSSSPTPTQGTGAGGGLHDKFMAKGKTYFGTEIDNYHLNNAP-LLAIAKS   116
Xyl3    GSEPQPSSTQGGTPQPTGGNSGGTGLDAKFKAKGKQYFGTEIDHYHLNNNP-LINIVKA    116
Ffam1   GSEPQPSSTQGGTPQPTGGNSGGTGLDAKFKAKGKQYFGTEIDHYHLNNNP-LINIVKA    116
XynA    ------HVLSEPIEPRQASVSIDSKFKAHGKKYLGNIGDQYTLTKNSKTPAVIKA        64
FIa     ------NVLANPIEPRQASVSIDAKFKAHGKKYLGTIGDQYTLNKNAKTPAIIKA        64
Xylnc   ------LATAAVLPRQ-SASLNDLFVAAGKSYFGTCSDQALLQNSQ-NEAIVAS        61
Pxyn    ------QALSGPVESRQASESIDAKFKAHGKKYLGNIADQGTLNGNPKTPAIIKA        68
Xyla    ------ALTAAGLLVTAAPAQAESTLRELAAQNGGRHFGTAIAYSPLNSDAQYRNIAAT    75
```

Fig. 3A

| | | |
|---|---|---|
| Cxy1 | SFGQVTCENSMKWDATEPRRGTFNFGNADSVVNWATSNGKLVRGHTLLWHSQLPSWVTQI | 176 |
| Xy13 | QFGQVTCENSMKWDAIEPSRNSFTFSNADKVVDFATQNGKLIRGHTLLWHSQLPQWVQNI | 176 |
| Ffam1 | QFGQVTCENSMKWDAIEPSRNSFTFSNADKVVDFATQNGKLIRGHTLLWHSQLPQWVQNI | 176 |
| XynA | DFGALTPENSMKWDATEPSRGQFSFSGSDYLVNFAQSNNKLIRGHTLVWHSQLPSWVQAI | 124 |
| FIa | DFGQLTPENSMKWDATEPNRGQFSFSGSDYLVNFAQSNGKLIRGHTLVWHSQLPSWVQSI | 124 |
| Xylnc | QFGVITPENSMKWDALEPSQGNFGWSGADYLVDYATQHNKKVRGHTLVWHSQLPSWVSSI | 121 |
| Pxyn | NFGQLSPENSMKWDATEPSQGQFSFAGSDYFVEFAETNGKLIRGHTLVWHSQLPSWVSSI | 128 |
| Xyla | QFSAITHENEMKWESLEPQRGQYNWSQADNIINFAKANNQIVRGHTLVWHSQLPSWLNNG | 135 |
| Cxy1 | SDR-TTLTSVIENHVTQMVTHYKGKILQWDVVN-EIFAEDGNLRDSVFSRVLGEDFVGIAF | 235 |
| Xy13 | NDR-STLTAVIENHVKTMVTRYKGKILQWDVVN-EIFAEDGNLRDSVFSRVLGEDFVGIAF | 235 |
| Ffam1 | NDR-STLTAVIENHVKTMVTRYKGKILQWDVVNNEIFAEDGNLRDSVFSRVLGEDFVGIAF | 236 |
| XynA | TDK-NTLIEVMKNHITTVMQHYKGKIYAWDVVN-EIFNEDGSLRDSVFYKVIGDDYVRIAF | 183 |
| FIa | YDK-GTLIQVMQNHIATVMQRYKGKVYAWDVVN-EIFNEDGSLRQSHFYNVIGEDYVRIAF | 183 |
| Xylnc | GDA-NTLRSVMTNHINEVVGRYKGKIMHWDVVN-EIFNEDGTFRNSVFYNLLGEDFVRIAF | 180 |
| Pxyn | TDK-TTLTDVMKNHITTVMKQYKGKLYAWDVVN-EIFEEDGTLRDSVFSRVLGEDFVRIAF | 187 |
| Xyla | GFSGSQLRSIMENHIEVVAGRYRGDVYAWDVVN-EAFNEDGTLRDSIWYRGMGRDYIAHAF | 195 |

Fig. 3B

```
Cxy1   RAARAADPNAKLYINDYNLDIANYAKVTKGMVEHVNKWVSQGIPIDGIGSQAHLAAPGGW   295
Xyl3   RAARAADPAAKLYINDYNLDKSDYAKLTRGMVAHVNKWIAAGIPIDGIGSQGHLAAPSGW   295
Ffam1  RAARAADPAAKLYINDYNLDKSDYAKLTRGMVAHVNKWIAAGIPIDGIGSQGHLAAPSGW   296
XynA   ETARAADPNAKLYINDYNLDSASYPKLAG-MVSHVKKWIEAGIPIDGIGSQTHLSAGGGA   242
FIa    ETARAVDPNAKLYINDYNLDSASYPKLTG-LVNHVKKWVAAGVPIDGIGSQTHLSAGAGA   242
Xylnc  ETARAADPDAKLYINDYNLDSASYAKTQA-MASYVKKWLAEGVPIDGIGSQAHYSSSHWS   239
Pxyn   ETAREADPEAKLYINDYNLDSATSAKLQG-MVSHVKKWIAAGVPIDGIGSQTHLGAGAGA   246
Xyla   RKAHEVDPDAKLYINDYNIEG-INAKSNG-LYNLVVDLLRDGVPIHGIGIQSHLIVGQVP   253

Cxy1   NSASGVPNALKTLAGANVKEIAVTELDIVG------ASANDYLTVMNGCLAVPKCV      345
Xyl3   NPASGVPAALRALAASDAKEIAITELDISG------ASANDYLTVMNACLAVPKCV      345
Ffam1  NPASGVPAALRALAASDAKEIAITELDISG------ASANDYLTVMNACLAVPKCV      346
XynA   GISG----ALNALAGAGTKEIAVTELDIAG------ASSTDYVEVVEACLDQPKCI      288
FIa    AVSG----ALNALAGAGTKEVAITELDIAG------ASSTDYVNVVKACLNQPKCV      288
Xylnc  STEAAG--ALSSLANTGVSEVAITELDIAG------AASSDYLNLLNACLNEQKCV      287
Pxyn   AASG----ALNALASASAGTEEVAVTELDIAG-----ATSTDYVDVVNACLDQPKCV     292
Xyla   STFQQN--IQRFADLG-LDVAITELDIRMQMPADQYKLQQQARDYEAVVNACLAVTRCI   299
```

Fig. 3C

```
Cxyl   GITVWGVSDKDSWRSSDSP----LLFDSNYNAK------QAYTTLLNAL-           384
Xyl3   GITVWGVSDKDSWRPGENP----LLYDSNYQPK------AAFNALVNAL-           384
Ffam1  GITVWGVSDKDSWRPGDNP----LLYDSNYQPK------AAFNALANAL-           385
XynA   GITVWGVADPDSWRSSSTP----LLFDSNYNPK------PAYTAIANAL-           327
FIa    GITVWGVADPDSWRSSSSP----LLFDSNYNPK------AAYTAIANAL-           327
Xylnc  GITVWGVSDKDSWRASDSP----LLFDGNYQPK------DAYNAIVNALS           327
Pxyn   GITVWGVADPDSWRADESP----LLFDASYNPKEAYNVSQLLSRQHAFDLYLKLGNLLL   347
Xyla   GITVWGIDDERSWVPYTFPGEGAPLLYDGQYNRK------PAWYAVYEALG           344

Cxyl   ---------------------------------------
Xyl3   ---------------------------------------
Ffam1  ---------------------------------------
XynA   ---------------------------------------
FIa    ---------------------------------------
Xylnc  ---------------------------------------
Pxyn   SRLHSD---------------------------------                       353
Xyla   GDSSGGGPEPGGPGGPEPGGPGGPGDGTCAVNYTVVNDWGHGMQGAITVSNTGSSPINNWT 404
```

Fig. 3D

```
Cxy1   ----------------------------------------------------------------
Xy13   ----------------------------------------------------------------
Ffam1  ----------------------------------------------------------------
XynA   ----------------------------------------------------------------
FIa    ----------------------------------------------------------------
Xylnc  ----------------------------------------------------------------
Pxyn   ----------------------------------------------------------------
Xyla   LQFSFSGVNISNGWNGEWSQSGSQITVRAPAWNSTLQPGQSVELGFVADKTGNVSPPSQF 464

Cxy1   ------
Xy13   ------
Ffam1  ------
XynA   ------
FIa    ------
Xylnc  ------
Pxyn   ------
Xyla   TLNGATCS 468
```

Fig. 3E

SEQUENCE LISTING

```
<160> NUMBER OF SEQ ID NOS: 7

<210> SEQ ID NO 1
<211> LENGTH: 1269
<212> TYPE: DNA
<213> ORGANISM: Coniothyrium minitans
<220> FEATURE:
<221> NAME/KEY: CDS
<222> LOCATION: (25)..(1179)
<220> FEATURE:
<221> NAME/KEY: misc_feature
<222> LOCATION: (88)..(180)
<223> OTHER INFORMATION: Cellulose-binding domain
<220> FEATURE:
<221> NAME/KEY: misc_feature
<222> LOCATION: (181)..(273)
<223> OTHER INFORMATION: hinge region
<220> FEATURE:
<221> NAME/KEY: misc_feature
```

```
<222> LOCATION: (274)..(1179)
<223> OTHER INFORMATION: catalytic domain
<220> FEATURE:
<221> NAME/KEY: misc_feature
<222> LOCATION: (25)..(75)
<223> OTHER INFORMATION: putative signal peptide

<400> SEQUENCE: 1
```

| | | | | | | | | | | | | | | | | |
|---|---|---|---|---|---|---|---|---|---|---|---|---|---|---|---|---|
| cccgtctgca | tcatctctgc | catc | atg | cgt | acc | tct | gtc | ctc | gcc | ctc | ata | | | | | 51 |
| | | | Met | Arg | Thr | Ser | Val | Leu | Ala | Leu | Ile | | | | | |
| | | | 1 | | | | 5 | | | | | | | | | |

| atc | gcc | ccc | act | gcc | gtg | ttc | ggt | cag | tcc | cag | ctt | tgg | agc | cag | tgt | 99 |
|---|---|---|---|---|---|---|---|---|---|---|---|---|---|---|---|---|
| Ile | Ala | Pro | Thr | Ala | Val | Phe | Gly | Gln | Ser | Gln | Leu | Trp | Ser | Gln | Cys | |
| 10 | | | | | 15 | | | | | 20 | | | | | 25 | |

| ggt | ggc | aat | gga | tgg | tcc | ggg | cct | acg | act | tgt | gtt | tcc | gga | tcg | gtg | 147 |
|---|---|---|---|---|---|---|---|---|---|---|---|---|---|---|---|---|
| Gly | Gly | Asn | Gly | Trp | Ser | Gly | Pro | Thr | Thr | Cys | Val | Ser | Gly | Ser | Val | |
| | | | 30 | | | | | 35 | | | | | 40 | | | |

| tgt | agc | aaa | gtg | aat | gac | tgg | tac | ttc | cag | tgt | att | cct | ggc | tcg | ggc | 195 |
|---|---|---|---|---|---|---|---|---|---|---|---|---|---|---|---|---|
| Cys | Ser | Lys | Val | Asn | Asp | Trp | Tyr | Phe | Gln | Cys | Ile | Pro | Gly | Ser | Gly | |
| | | 45 | | | | | 50 | | | | | 55 | | | | |

| ggg | gga | tct | cca | gct | ccc | acc | act | acc | gcc | gca | gga | agc | agc | cct | act | 243 |
|---|---|---|---|---|---|---|---|---|---|---|---|---|---|---|---|---|
| Gly | Gly | Ser | Pro | Ala | Pro | Thr | Thr | Thr | Ala | Ala | Gly | Ser | Ser | Pro | Thr | |
| | 60 | | | | | 65 | | | | | 70 | | | | | |

| ccc | acc | cag | ggc | aca | ggg | gcc | gga | ggt | ggt | cta | cac | gac | aag | ttc | atg | 291 |
|---|---|---|---|---|---|---|---|---|---|---|---|---|---|---|---|---|
| Pro | Thr | Gln | Gly | Thr | Gly | Ala | Gly | Gly | Gly | Leu | His | Asp | Lys | Phe | Met | |
| 75 | | | | | 80 | | | | | 85 | | | | | | |

| gcc | aag | ggc | aag | acc | tac | ttc | ggt | act | gag | atc | gac | aac | tac | cat | ctg | 339 |
|---|---|---|---|---|---|---|---|---|---|---|---|---|---|---|---|---|
| Ala | Lys | Gly | Lys | Thr | Tyr | Phe | Gly | Thr | Glu | Ile | Asp | Asn | Tyr | His | Leu | |
| 90 | | | | | 95 | | | | | 100 | | | | | 105 | |

| aac | aac | gcc | cct | ttg | ctg | gct | atc | gcc | aaa | agc | agc | ttt | ggt | cag | gtc | 387 |
|---|---|---|---|---|---|---|---|---|---|---|---|---|---|---|---|---|
| Asn | Asn | Ala | Pro | Leu | Leu | Ala | Ile | Ala | Lys | Ser | Ser | Phe | Gly | Gln | Val | |
| | | | 110 | | | | | 115 | | | | | 120 | | | |

| aca | tgc | gag | aac | agc | atg | aaa | tgg | gat | gcc | acg | gaa | ccg | cga | cgt | gga | 435 |
|---|---|---|---|---|---|---|---|---|---|---|---|---|---|---|---|---|
| Thr | Cys | Glu | Asn | Ser | Met | Lys | Trp | Asp | Ala | Thr | Glu | Pro | Arg | Arg | Gly | |
| | | 125 | | | | | 130 | | | | | 135 | | | | |

| aca | ttc | aac | ttc | ggc | aac | gct | gat | tcc | gtc | gtc | aac | tgg | gcc | acg | tcg | 483 |
|---|---|---|---|---|---|---|---|---|---|---|---|---|---|---|---|---|
| Thr | Phe | Asn | Phe | Gly | Asn | Ala | Asp | Ser | Val | Val | Asn | Trp | Ala | Thr | Ser | |
| | 140 | | | | | 145 | | | | | 150 | | | | | |

| aac | gga | aag | ctc | gtc | cgt | ggc | cac | acc | ctc | ctt | tgg | cac | agc | cag | ttg | 531 |
|---|---|---|---|---|---|---|---|---|---|---|---|---|---|---|---|---|
| Asn | Gly | Lys | Leu | Val | Arg | Gly | His | Thr | Leu | Leu | Trp | His | Ser | Gln | Leu | |
| 155 | | | | | 160 | | | | | 165 | | | | | | |

| ccg | agc | tgg | gtc | acc | cag | atc | agt | gac | cgc | aca | aca | ttg | aca | tcc | gtc | 579 |
|---|---|---|---|---|---|---|---|---|---|---|---|---|---|---|---|---|
| Pro | Ser | Trp | Val | Thr | Gln | Ile | Ser | Asp | Arg | Thr | Thr | Leu | Thr | Ser | Val | |
| 170 | | | | | 175 | | | | | 180 | | | | | 185 | |

| atc | gaa | aac | cac | gtg | aca | cag | atg | gtc | acg | cat | tac | aag | ggc | aag | att | 627 |
|---|---|---|---|---|---|---|---|---|---|---|---|---|---|---|---|---|
| Ile | Glu | Asn | His | Val | Thr | Gln | Met | Val | Thr | His | Tyr | Lys | Gly | Lys | Ile | |
| | | | 190 | | | | | 195 | | | | | 200 | | | |

| ctc | caa | tgg | gat | gta | gtt | aat | gag | atc | ttc | gcc | gag | gat | ggt | aac | ctc | 675 |
|---|---|---|---|---|---|---|---|---|---|---|---|---|---|---|---|---|
| Leu | Gln | Trp | Asp | Val | Val | Asn | Glu | Ile | Phe | Ala | Glu | Asp | Gly | Asn | Leu | |
| | | 205 | | | | | 210 | | | | | 215 | | | | |

| cga | gac | agc | gtc | ttc | agc | cgt | gtg | ctc | ggc | gag | gac | ttc | gtt | ggc | atc | 723 |
|---|---|---|---|---|---|---|---|---|---|---|---|---|---|---|---|---|
| Arg | Asp | Ser | Val | Phe | Ser | Arg | Val | Leu | Gly | Glu | Asp | Phe | Val | Gly | Ile | |
| | 220 | | | | | 225 | | | | | 230 | | | | | |

| gcc | ttc | cgc | gct | gct | cgc | gcc | gcc | gat | cct | aac | gcg | aag | ctc | tac | att | 771 |
|---|---|---|---|---|---|---|---|---|---|---|---|---|---|---|---|---|
| Ala | Phe | Arg | Ala | Ala | Arg | Ala | Ala | Asp | Pro | Asn | Ala | Lys | Leu | Tyr | Ile | |
| 235 | | | | | 240 | | | | | 245 | | | | | | |

| aat | gat | tat | aac | ctc | gac | atc | gca | aac | tat | gca | aag | gtg | acc | aaa | ggc | 819 |
|---|---|---|---|---|---|---|---|---|---|---|---|---|---|---|---|---|
| Asn | Asp | Tyr | Asn | Leu | Asp | Ile | Ala | Asn | Tyr | Ala | Lys | Val | Thr | Lys | Gly | |
| 250 | | | | 255 | | | | | 260 | | | | | 265 | | |

| atg | gtc | gag | cac | gtc | aac | aaa | tgg | gtg | tcg | cag | ggc | atc | ccc | atc | gac | 867 |
|---|---|---|---|---|---|---|---|---|---|---|---|---|---|---|---|---|
| Met | Val | Glu | His | Val | Asn | Lys | Trp | Val | Ser | Gln | Gly | Ile | Pro | Ile | Asp | |

-continued

```
              270                 275                 280 ggc atc ggc tcg cag gcc cat ctt gca gca ccc ggt ggg tgg aac tcg      915
Gly Ile Gly Ser Gln Ala His Leu Ala Ala Pro Gly Gly Trp Asn Ser
            285                 290                 295 gcg tct ggc gtt ccc aac gca ctc aag acg ctg gcc ggc gcc aac gtc      963
Ala Ser Gly Val Pro Asn Ala Leu Lys Thr Leu Ala Gly Ala Asn Val
        300                 305                 310 aaa gag atc gcc gtc act gag ctc gac att gtc ggc gcg tcg gca aac     1011
Lys Glu Ile Ala Val Thr Glu Leu Asp Ile Val Gly Ala Ser Ala Asn
    315                 320                 325 gac tac ctc acc gtc atg aac ggc tgt ctc gcc gtg ccc aag tgc gtc     1059
Asp Tyr Leu Thr Val Met Asn Gly Cys Leu Ala Val Pro Lys Cys Val
330                 335                 340                 345 ggt att act gtt tgg ggt gtc tcc gac aag gac agc tgg cgc agt agc     1107
Gly Ile Thr Val Trp Gly Val Ser Asp Lys Asp Ser Trp Arg Ser Ser
                350                 355                 360 gac agc cct ctg ctg ttc gac agc aac tac aat gcc aag cag gcg tac     1155
Asp Ser Pro Leu Leu Phe Asp Ser Asn Tyr Asn Ala Lys Gln Ala Tyr
            365                 370                 375 acc aca ctg ctc aac gcg ttg taa aggattctgg agacaatcgg tcgtagtatt    1209
Thr Thr Leu Leu Asn Ala Leu
        380                 385 aggatagatt aaatcatgct tgccagcagg taataaagcc gaaaaaaaaa aaaaaaaaaa   1269

<210> SEQ ID NO 2
<211> LENGTH: 384
<212> TYPE: PRT
<213> ORGANISM: Coniothyrium minitans

<400> SEQUENCE: 2

Met Arg Thr Ser Val Leu Ala Leu Ile Ile Ala Pro Thr Ala Val Phe
  1               5                  10                  15

Gly Gln Ser Gln Leu Trp Ser Gln Cys Gly Gly Asn Gly Trp Ser Gly
            20                  25                  30

Pro Thr Thr Cys Val Ser Gly Ser Val Cys Ser Lys Val Asn Asp Trp
        35                  40                  45

Tyr Phe Gln Cys Ile Pro Gly Ser Gly Gly Gly Ser Pro Ala Pro Thr
    50                  55                  60

Thr Thr Ala Ala Gly Ser Ser Pro Thr Pro Thr Gln Gly Thr Gly Ala
 65                  70                  75                  80

Gly Gly Gly Leu His Asp Lys Phe Met Ala Lys Gly Lys Thr Tyr Phe
                85                  90                  95

Gly Thr Glu Ile Asp Asn Tyr His Leu Asn Asn Ala Pro Leu Leu Ala
            100                 105                 110

Ile Ala Lys Ser Ser Phe Gly Gln Val Thr Cys Glu Asn Ser Met Lys
        115                 120                 125

Trp Asp Ala Thr Glu Pro Arg Arg Gly Thr Phe Asn Phe Gly Asn Ala
    130                 135                 140

Asp Ser Val Val Asn Trp Ala Thr Ser Asn Gly Lys Leu Val Arg Gly
145                 150                 155                 160

His Thr Leu Leu Trp His Ser Gln Leu Pro Ser Trp Val Thr Gln Ile
                165                 170                 175

Ser Asp Arg Thr Thr Leu Thr Ser Val Ile Glu Asn His Val Thr Gln
            180                 185                 190

Met Val Thr His Tyr Lys Gly Lys Ile Leu Gln Trp Asp Val Val Asn
        195                 200                 205
```

-continued

```
Glu Ile Phe Ala Glu Asp Gly Asn Leu Arg Asp Ser Val Phe Ser Arg
    210                 215                 220

Val Leu Gly Glu Asp Phe Val Gly Ile Ala Phe Arg Ala Ala Arg Ala
225                 230                 235                 240

Ala Asp Pro Asn Ala Lys Leu Tyr Ile Asn Asp Tyr Asn Leu Asp Ile
                245                 250                 255

Ala Asn Tyr Ala Lys Val Thr Lys Gly Met Val Glu His Val Asn Lys
            260                 265                 270

Trp Val Ser Gln Gly Ile Pro Ile Asp Gly Ile Gly Ser Gln Ala His
        275                 280                 285

Leu Ala Ala Pro Gly Gly Trp Asn Ser Ala Ser Gly Val Pro Asn Ala
    290                 295                 300

Leu Lys Thr Leu Ala Gly Ala Asn Val Lys Glu Ile Ala Val Thr Glu
305                 310                 315                 320

Leu Asp Ile Val Gly Ala Ser Ala Asn Asp Tyr Leu Thr Val Met Asn
                325                 330                 335

Gly Cys Leu Ala Val Pro Lys Cys Val Gly Ile Thr Val Trp Gly Val
            340                 345                 350

Ser Asp Lys Asp Ser Trp Arg Ser Ser Asp Ser Pro Leu Leu Phe Asp
        355                 360                 365

Ser Asn Tyr Asn Ala Lys Gln Ala Tyr Thr Thr Leu Leu Asn Ala Leu
    370                 375                 380

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence:
      Semi-degenerate PCR forward primer Ff1

<400> SEQUENCE: 3
gagaayagca tgaartggga ygc                                              23

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence:
      Semi-degenerate PCR forward primer Ff5

<400> SEQUENCE: 4
acygtctggg gwgtbdcyga c                                                21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence:
      Semi-degenerate PCR reverse primer Fr5

<400> SEQUENCE: 5
gtcrghvacw ccccagacrg t                                                21

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:
```

-continued

```
   PCR forward primer Ff1b

<400> SEQUENCE: 6
gacgtggaac attcaacttc                                              20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:
      PCR reverse primer Fr5b

<400> SEQUENCE: 7
ttcatgacgg tgaggtagtc                                              20
```

CONIOTHYRIUM MINITANS XYLANASE GENE CXY1

FIELD OF THE INVENTION

The invention pertains to a xylanase gene of *Coniothyrium minitans*.

BACKGROUND OF THE INVENTION

The walls of plant cells are formed of cellulose, hemicellulose, and lignin polymers, which contribute to cell wall structure and rigidity. These complex carbohydrates act as a physical barrier to infection by plant pathogens, and are necessary to prevent dehydration and maintain physical integrity. Xylan, a polymeric chain of xylose carbohydrate monomers linked by successive β-1,4 xylose linkages, constitutes a significant portion of plant hemicellulose. Xylan contributes to the tensile strength of plant secondary walls, and functions to limit the accessibility of cellulases to the cell wall, thereby preventing damage to the plant surface by challenge of plant pathogens.

The degradation of plant tissues involves, in part, the hydrolysis of xylan by enzymes produced by fibrolytic bacteria and fungi. The physical structure of xylan is complex, and its degradation is accomplished by a consortium of hydrolytic enzymes. Substituent-free β-1,4 xylan polymers are digested into shorter oligoxylan fragments by endoxylanlolytic enzymes (EC 3.2.1.8), and the resulting oligoxylan fragments are subsequently degraded into xylose monomers by β-xylosidases (EC 3.2.1.37) (Bieley, 1985). However, the hydrolysis of xylan is complicated by the presence of various substituents (such as acetyl, arabinosyl, and glucuranosyl) along the elongated β-1,4 xylose chains. The prevalence of various substituent groups on xylan polymers varies amongst differing plant types. Xylan derived from grasses appear to predominantly contain arabinose constituents, whereas xylan polymers derived from hardwoods contain acetyl and arabinose substituents. These substituents attached to the β-1,4 xylan backbone obstruct endoxylanolytic hydrolysis by steric impediment of the xylanase enzymes. Xylanolytic degradation is therefore effected by xylanases in concert with enzymes such as α-L-arabinofuranosidases (EC 3.2.1.55) and acetylesterases (EC 3.1.1.6), which cleave substituents from the xylan polymer.

Xylanolytic enzymes have numerous applications in industry and biotechnology. Such applications include the supplementation of xylanases in biopulping processes. For example, pulp quality may be improved by the enzymatic removal of xylan from woody plant tissue. Predigestion of forage crops with cellulases and xylanases can improve nutritional availability of feed carbohydrates and enhance fermentative composting. Furthermore, xylanases may be employed to degrade agricultural wastes, thereby reducing organic waste disposal in landfill sites. Xylanases have also been used to improve the quality of flour in baked goods. Because xylan represents a considerable reserve of nutritive sugar sequestered in plant biomass, xylanases are important in ruminal digestion of forage fiber, where the release of xylose monomers may provide a nutritive source for non-xylanolytic ruminal microflora.

Given the industrial importance of xylanases, there is great interest in isolating new, highly active xylanases that can be produced inexpensively. Ideally, such enzymes should be active over broad temperature and pH ranges, and are preferably functional in both prokaryotic and eukaryotic expression systems.

A range of microorganisms produce xylanases, and from these a number of xylanase genes have been isolated. Xylanase genes can be categorized into two main families, 10 (clan GH-A, previously F family of glycosyl hydrolases) and 11 (clan GH-C, previously G family of glycosyl hydrolases) (Henrissat et al., 1989; Henrissat and Bairoch, 1993). Many microbial xylanases have been identified in the literature. Fungal xylanases originating from Aspergillus species (Arai et al. 1998, Ito et al. 1992), *Emericella nidulans* (MacCabe et al. 1996, previously identified as *Aspergillus nidulans*), and *Penicillium chrysogenum* (Haas et al. 1993) contain a catalytic domain which appears to be conserved among these species and encode polypeptides containing between 327 and 347 amino acids. Xylanases originating from *Fursarium oxysporum* (Ruiz-Roldan et al., 1998; Sheppard et al., 1994) contain a conserved catalytic domain and, additionally, a cellulose binding domain and a linker or hinge domain attaching the cellulose binding domain to the catalytic domain. With the additional domains, the polypeptides contain 384 amino acids. U.S. Pat. No. 5,763,254 to Woldike et al. discloses the DNA sequences and derived amino acid sequences of *F. oxysporum* C-family cellobiohydrolase, *F. oxysporum* F-family cellulase, *F. oxysporum* C-family endoglucanase, and *Humicola insolens* endoglucanase 1, each of which possess a carbohydrate binding domain, a linker region, and a catalytic domain.

The fungus *Coniothyrium minitans* Campbell is a mycoparasite capable of attacking the fungal plant pathogen *Sclerotinia sclerotiorum* (Lib) de Bary (Huang and Hoes, 1976), resulting in the degradation of sclerotia (Huang and Kokko, 1987) and hyphae (Huang and Kokko, 1988) of the pathogen. Jones et al. (1974) reported endo- and exo-1,3-β-glucanase activity in *C. minitans.* International application No. PCT/CA98/00668 discloses strains of *C. minitans* having high levels of β-glucanase activity when grown by liquid or solid state fermentation. However, the prior art has not looked to *C. minitans* as a source for the isolation of xylanase genes.

SUMMARY OF THE INVENTION

The invention provides a novel xylanase gene (denoted herein as cxy1) of the soil borne fungus *Coniothyrium minitans.* The DNA sequence of the cxy1 gene and the amino acid sequence of the encoded xylanase Cxy1 are depicted in SEQ ID NOS: 1 and 2, respectively. The cxy1 gene is compatible with both eukaryotic and prokaryotic expression systems, making it particularly useful for a wide range of industrial applications, including, without limitation, the improvement of nutritional availability of carbohydrates in animal feeds.

Encoded xylanase Cxy1 is specific for xylan substrates, and no activity has been measured on other substrates such as carboxymethylcellulose ("CMC"), barley β-glucan, lichenan, or laminarin. The pH and temperature optima for xylanase Cxy1 are 7.5–8.0 and 47° C., respectively. Cxy1 contains 384 amino acids, and has a predicted pl of 6.0, and a molecular weight of 40,945.

BRIEF DESCRIPTION OF THE DRAWINGS

FIGS. 1A and 1B are a sequence alignment comparison of several F-family fungal xylanase genes used in construction of the semi-degenerate xylanase-specific PCR primers used in the invention. Sources for xylanase sequences are: (1) *Fursarium oxysporum* (Sheppard et al., 1994; GenBank accession no. L29380); (2) *Aspergillus aculeatus* (Arai et al., 1998; GenBank accession no. AB013110); (3) *Emericella nidulans* (MacCabe et al., 1996; GenBank accession no. Z49894); and (4) *Humicola grisea* (Iikura et al., 1997; GenBank accession no. AB001030).

FIGS. 2A, 2B and 2C depict the nucleotide sequence of the *C. minitans* cxy1 xylanase gene (SEQ ID NO: 1) and the deduced amino acid sequence of the encoded Cxy1 xylanase (SEQ ID NO: 2). The open reading frame is indicated by the corresponding amino acids underneath (extending from nucleotide 25 to 1179). The carbohydrate-binding domain extending from nucleotide 88 to 180 is indicated in boldface, the linker region located from nucleotide 181 to 273 is indicated by the italic letters, and the catalytic domain extending from nucleotide 274 to 1179 is underlined.

FIGS. 3A–3E are a sequence comparison of *C. minitans* xylanase Cxy1 (SEQ ID NO: 2) with representative fungal and bacterial xylanases. Sequences were aligned using the ClustalW alignment algorithm. Conserved amino-acid residues are highlighted in bold. The representative xylanases depicted are as follows: Xyl3, *Fursarium oxysporum* (fungal phytopathogen, GenBank accession no. AF052582; Ruiz-Roldan et al., 1998); Ffaml, *Fusarium oxysporum* (fungal phytopathogen, GenBank accession no. L29380; Sheppard et al., 1994); XynA, *Aspergillus kawachii* (fungus, GenBank accession no. D14847; Ito et al., 1992); FIa, *Aspergillus aculeatus* (fungus, GenBank accession no. AB013110; Arai et al., 1998); Xylnc, *Emericella nidulans* (fungus, GenBank accession no. Z49894; MacCabe et al., 1996); Pxyn, *Penicillium chrysogenum* (fungus, GenBank accession no. M98458; Haas et al., 1993); Xyla, *Thermomonospora alba* (eubacteria, GenBank accession no. Z81013; Blanco et al., 1997).

DETAILED DESCRIPTION OF THE PREFERRED EMBODIMENTS

In order to provide a clear and consistent understanding of the specification and claims, including the scope to be given to such terms, the following definitions are provided.

"Catalytic domain" means the region of the amino acid sequence of an enzyme that includes the catalytic site that provides the catalytic activity of the enzyme.

"Carbohydrate binding domain" means an amino acid sequence capable of effecting binding of the enzyme to a cellulose or hemicellulose substrate.

"Coding sequence" means the part of a gene which codes for the amino acid sequence of a protein, or for a functional RNA such as a tRNA or rRNA.

"Complement" or "complementary sequence" means a sequence of nucleotides which forms a hydrogen-bonded duplex with another sequence of nucleotides according to Watson-Crick base-pairing rules. For example, the complementary base sequence for 5'-AAGGCT-3"is 3'-TTCCGA-5'.

"Downstream" means on the 3' side of any site in DNA or RNA.

"Expression" refers to the transcription of a gene into structural RNA (rRNA, tRNA) or messenger RNA (mRNA) with subsequent translation into a protein.

An amino acid sequence that is "functionally equivalent" to *C. minitans* Cxy1 is an amino acid sequence that has been modified by single or multiple amino acid substitutions, by addition and/or deletion of amino acids, or where one or more amino acids have been chemically modified, but which nevertheless retains the xylanolytic activity of *C. minitans* Cxy1. "Functionally equivalent" nucleotide sequences are those that encode polypeptides having substantially the same biological activity.

Two nucleic acid sequences are "heterologous" to one another if the sequences are derived from separate organisms, whether or not such organisms are of different species, as long as the sequences do not naturally occur together in the same arrangement in the same organism.

"Hemicellulose" includes glucans (apart from starch), mannans, xylans, arabinans or polyglucuronic or polygalacturonic acid.

A "hemicellulose-degrading enzyme" is an enzyme that catalyzes the degradation of hemicellulose.

"Homology" refers to the extent of identity between two nucleotide or amino acid sequences.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Linker region" means an amino acid sequence that operably links two functional domains of an enzyme.

"Nucleic acid construct" means a nucleic acid molecule which is isolated from a naturally occurring gene or which has been modified to contain segments of nucleic acid which are combined and juxtaposed in a manner which would not otherwise exist in nature.

"Nucleic acid molecule" means a single- or double-stranded linear polynucleotide containing either deoxyribonucleotides or ribonucleotides that are linked by 3'-5'-phosphodiester bonds.

Two DNA sequences are "operably linked" if the nature of the linkage does not interfere with the ability of the sequences to effect their normal functions relative to each other. For instance, a promoter region would be operably linked to a coding sequence if the promoter were capable of effecting transcription of that coding sequence.

A "polypeptide" is a linear polymer of amino acids that are linked by peptide bonds.

"Promoter" means a cis-acting DNA sequence, generally 80–120 base pairs long and located upstream of the initiation site of a gene, to which RNA polymerase may bind and initiate correct transcription.

A "recombinant" nucleic acid molecule, for instance a recombinant DNA molecule, is a novel nucleic acid sequence formed in vitro through the ligation of two or more nonhomologous DNA molecules (for example a recombinant plasmid containing one or more inserts of foreign DNA cloned into its cloning site or its polylinker).

"Transformation" means the directed modification of the genome of a cell by the external application of purified recombinant DNA from another cell of different genotype, leading to its uptake and integration into the subject cell's genome. In bacteria, the recombinant DNA is not integrated into the bacterial chromosome, but instead replicates autonomously as a plasmid.

"Upstream" means on the 5' side of any site in DNA or RNA.

A "vector" is a nucleic acid molecule that is able to replicate autonomously in a host cell and can accept foreign DNA. A vector carries its own origin of replication, one or more unique recognition sites for restriction endonucleases which can be used for the insertion of foreign DNA, and usually selectable markers such as genes coding for antibiotic resistance, and often recognition sequences (e.g. promoter) for the expression of the inserted DNA. Common vectors include plasmid vectors and phage vectors.

"Xylanolytic activity" in the context of a polypeptide, means the ability of the polypeptide to catalyze the release of xylose from a substrate that contains xylan.

The invention provides a novel xylanase gene obtained from *Coniothyrium minitans*, and denoted cxy1. The nucleotide sequence of the cxy1 gene is set forth in SEQ ID NO: 1. The cxy1 gene encodes a polypeptide having xylanolytic activity, and denoted *C. minitans* xylanase Cxy1. The amino acid sequence of Cxy1 is depicted in SEQ ID NO: 2.

It will be appreciated by those of skill in the art that, due to the degeneracy of the genetic code, numerous functionally equivalent nucleotide sequences encode the same amino acid sequence. All nucleotide sequences that encode the Cxy1 xylanase sequence depicted in SEQ ID NO: 2 are included in the invention.

Further, strains of *C. minitans* may contain naturally occurring allelic variants of the cxy1 gene which encode variants of the Cxy1 xylanase having xylanolytic activity that is substantially the same as that of the Cxy1 sequence depicted in SEQ ID NO: 2. All such allelic variants of the cxy1 gene and the encoded Cxy1 xylanase are included within the scope of the invention.

Using the techniques described in detail in the Examples herein, the cxy1 gene sequence depicted in SEQ ID NO: 1 can be used to design primers (such as the Ff1/Fr5 primer pair described in the Examples herein) for amplification of homologous sequences in *C. minitans* or other organisms by polymerase chain reaction (PCR), or for the construction of labeled probes (e.g. biotin-labeled, radio-labeled) for use in nucleic acid hybridization assays to identify homologous nucleic acid sequences. Such sequences can then be tested by the methods described in the Examples herein for the expression of polypeptides having xylanolytic activity. By these methods, those of skill in the art can identify different alleles of the cxy1 xylanase gene, or variant nucleotide sequences that encode polypeptides having xylanolytic activity.

Additionally, those of skill in the art, through standard mutagenesis techniques, in conjunction with the xylanolytic activity assays described in the Examples herein, can obtain altered cxy1 gene sequences and test them for the expression of polypeptides having xylanolytic activity. Useful mutagenesis techniques known in the art include, without limitation, oligonucleotide-directed mutagenesis, region-specific mutagenesis, linker-scanning mutagenesis, and site-directed mutagenesis by PCR (see e.g. Sambrook et al., 1989 and Ausubel et al., 1999).

In obtaining variant cxy1 coding sequences, those of ordinary skill in the art will recognize that proteins may be modified by certain amino acid substitutions, additions, deletions, and post-translational modifications, without loss or reduction of biological activity. In particular, it is well-known that conservative amino acid substitutions, that is, substitution of one amino acid for another amino acid of similar size, charge, polarity and conformation, are unlikely to significantly alter protein function. The 20 standard amino acids that are the constituents of proteins can be broadly categorized into four groups of conservative amino acids as follows: the nonpolar (hydrophobic) group includes alanine, isoleucine, leucine, methionine, phenylalanine, proline, tryptophan and valine; the polar (uncharged, neutral) group includes asparagine, cysteine, glutamine, glycine, serine, threonine and tyrosine; the positively charged (basic) group contains arginine, histidine and lysine; and the negatively charged (acidic) group contains aspartic acid and glutamic acid. Substitution in a protein of one amino acid for another within the same group is unlikely to have an adverse effect on the biological activity of the protein.

As shown in FIGS. 3A and 3B, xylanase Cxy1 exhibits greatest homology to other F-family xylanases within the catalytic domain region. It is well-known in the art that individual amino acids or sequences of amino acids that are essential to the biological activity of a protein are closely conserved amongst related proteins, in accordance with principles of natural selection. Thus, those of skill in the art will recognize that substitutions, additions, deletions, and modifications of amino acids within the Cxy1 sequence at non-conserved regions will be less likely to negatively affect the xylanolytic function of the enzyme than would equivalent changes within highly conserved regions. As such, it is expected that substitutions, additions deletions, and modifications would be least likely to negatively affect the xylanolytic activity of Cxy1 if they were to occur in a subregion where there is little or no conservation of the amino acid sequence.

Homology between nucleotide sequences can be determined by DNA hybridization analysis, wherein the stability of the double-stranded DNA hybrid is dependent on the extent of base pairing that occurs. Conditions of high temperature and/or low salt content reduce the stability of the hybrid, and can be varied to prevent annealing of sequences having less than a selected degree of homology. For instance, for sequences with about 55% G - C content, hybridization and wash conditions of 40–50° C., 6 ×SSC (sodium chloride/sodium citrate buffer) and 0.1% SDS (sodium dodecyl sulfate) indicate about 60–70% homology, hybridization and wash conditions of 50–65° C., 1×SSC and 0.1% SDS indicate about 82–97% homology, and hybridization and wash conditions of 52° C., 0.1× SSC and 0.1% SDS indicate about 99–100% homology. A wide range of computer programs for comparing nucleotide and amino acid sequences (and measuring the degree of homology) are also available, and a list providing sources of both commercially available and free software is found in Ausubel el al. (1999). Readily available sequence comparison and multiple sequence alignment algorithms are, respectively, the Basic Local Alignment Search Tool (BLAST) (Altschul et al., 1997) and ClustalW programs. BLAST is available on the Internet at http://www.ncbi.nlm.nih.gov and a version of ClustalW is available at http://www2.ebi.ac.uk.

In view of the foregoing, nucleotide sequences having at least 80% homology, more preferably at least 85% homology, even more preferably at least 90% homology, and most preferably at least 95% homology with the cxy1 gene sequence depicted in SEQ ID NO: 1, and which encode polypeptides having xylanolytic activity are within the scope of this invention, as are amino acid sequences having at least 85%, more preferably at least 90%, and even more preferably at least 95% homology with the Cxy1 xylanase sequence depicted in SEQ ID NO: 2 and which possess xylanolytic activity. These homology values are based on comparison between the whole length of both sequences encoding a polypeptide at the amino acid or DNA level. Thus, in a first embodiment, the invention provides an isolated nucleic acid molecule encoding a polypeptide having xylanolytic activity, the encoded polypeptide comprising the amino acid sequence depicted in SEQ ID NO: 2 from amino acid 1 to amino acid 384, or a functionally equivalent sequence having at least 85% homology thereto.

As discussed in detail in Example 4 herein, analysis of the Cxy1 xylanase sequence depicted in SEQ ID NO: 2 indicates that Cxy1 has a structure that is typical of F-family fungal xylanases. Cxy1 also includes carbohydrate binding and linker domains, structures that have been identified in F-family fungal xylanases found in *F. oxysporum, Trichoderma reesei*, and *Phanerochaete chrysosporium*. The portion of SEQ ID NO: 2 from amino acid 1 through amino acid 17 exhibits the characteristics of a signal peptide as suggested by analysis of the sequence (Nielsen et al., 1997). It is believed that deletion of the region of the Cxy1 amino acid sequence from amino acid 1 through amino acid 22 should not negatively affect the xylanolytic activity of the enzyme, but may affect where the enzyme is targeted. Therefore, in another embodiment, the invention provides an isolated nucleic acid molecule encoding a polypeptide having xylanolytic activity, the encoded polypeptide comprising the amino acid sequence depicted in SEQ ID NO: 2 from amino acid 22 to amino acid 384, or a functionally equivalent sequence having at least 85% homology thereto.

The segment of SEQ ID NO: 2 from amino acid 23 through amino acid 52 is a sequence that is characteristic of a carbohydrate-binding domain ("CBD"), which functions to tether cellulolytic or hemicellulolytic enzymes to a cellulose or hemicellulose substrate. The segment of SEQ ID NO: 2 from amino acid 53 through amino acid 83 is a sequence that is characteristic of a linker or hinge region, and may function in coordinating the teriary structure of the carbohydrate-binding domain and the catalytic domain during xylan catalysis.

The catalytic domain comprises amino acids 84 through 384 of SEQ ID NO: 2. The Cxy1 catalytic domain contains numerous discrete regions of homology with the catalytic domains of xylanases from fungal organisms from the genera Aspergillus, Penicillium, Emericella, and many other species (see FIGS. 3A through 3E). For example, the 17 amino acids at positions 343–359 have 88–100% identity (15–17 identical amino acids) with the other xylanases depicted. The 14 amino acids at positions 242–255 have 93–100% identity (13 or 14 identical amino acids) with the other xylanases depicted. The 11 amino acids at positions 124–134 have 91–100% identity (10 or 11 identical amino acids) with the other xylanases depicted.

At the active site of a xylanase, the enzymatic hydrolysis of the glycosidic bond takes place via general acid catalysis that requires two critical residues: a proton donor and a nucleophile/base (Davies and Henrissat, 1995). This hydrolysis occurs via two major mechanisms, giving rise to either an overall retention, or an inversion, of anomeric configuration. The two amino acid residues of Cxy1 that act as the proton donor and the nucleophile/base appear to be Glu 209 and Glu 320. Comparison to other xylanases can be made at http://expasy.hcuge.ch. There are discrete regions of near-identical or identical conservation of amino acids around these two Glu residues in the xylanases depicted in FIGS. 3A–3E. Seven or eight amino acids out of eight are identical in positions 204–211 (88–100% identity) and six or seven amino acids out of seven are identical in positions 317–323 (86–100% identity).

These other xylanases contain only a catalytic domain, and do not contain carbohydrate binding domains or linker regions. As these other xylanases have activity with only a catalytic domain, and because of the discrete regions of homology with the Cxy1 catalytic domain, it is believed that the Cxy1 catalytic domain would exhibit xylanolytic activity independent from its associated carbohydrate binding domain and linker region. Therefore, in a further embodiment, the invention provides an isolated nucleic acid molecule encoding a polypeptide having xylanolytic activity, the encoded polypeptide comprising the amino acid sequence depicted in SEQ ID NO: 2 from amino acid 84 to amino acid 384 or a functionally equivalent sequence having at least 85% homology thereto.

The carbohydrate binding domain and linker region of Cxy1 (amino acids 23–83 of SEQ ID NO: 2) likely enhance the stability and activity of the Cxy1 catalytic domain. It is believed they would also enhance the stability and activity of other xylanase catalytic domains, or those of other hemicellulose-degrading enzymes, if operably linked to such catalytic domains. Therefore, in another embodiment, the invention extends to a nucleic acid molecule encoding the Cxy1 carbohydrate-binding domain and linker region (the amino acid sequence depicted in SEQ ID NO: 2 from amino acid 23 to amino acid 83), or a functionally equivalent sequence having at least 80% homology thereto. The invention further extends to a nucleic acid construct comprising this nucleic acid molecule operably linked to a nucleic acid molecule that encodes a catalytic domain of a hemicellulose-degrading enzyme and that is heterologous to this nucleic acid molecule.

The functional compatibility of cxy1 with prokaryotic expression systems such as *E. coli* (see Example 5 herein) is of great importance to application of the Cxy1 xylanase in biotechnological and agricultural industries. *C. minitans* is a higher eukaryotic fungus, belonging to either the Ascomycota or Basidiomycota subphyla, depending on its reproductive regimen. Thus, the cxy1 gene is likely to be compatible with other higher eukaryotic systems (such as eukaryotic plant or yeast expression systems) for mass production, and useful as a possible resistance gene to phytopathogens such as *S. sclerotiorum*. Example 6 herein describes the expression of cxy1 in a eukaryotic system, namely *Pichea pastoris*. However, functional compatibility of cxy1 with microbial systems is also of great importance to ruminal biotechnology. The transfer of the cxy1 cDNA into non-xylanolytic ruminal microbes or lower ruminal fungi, and the overexpression of cxy1 in the rumen can increase digestive efficiency of xylan-rich forage fiber in ruminant animals. Therefore, in further embodiments, the invention extends to cells other than *C. minitans* transformed with a nucleic acid molecule encoding *C. minitans* xylanase Cxy1 or a variant thereof having xylanolytic activity, as discussed above, and to methods for producing a polypeptide having xylanolytic activity, comprising culturing such cells under conditions conducive to the expression of the encoded polypeptide and recovering the encoded polypeptide from the culture. The invention also extends to vectors containing nucleic acid molecules of the invention encoding polypeptides having xylanolytic activity. Such vectors will usually also contain at least a promoter and a transcription termination signal.

Industrial strains of microorganisms (e.g., *Aspergillus niger, Aspergillus ficuum, Aspergillus awamori, Aspergillus oryzae, Trichoderma reesei, Mucor miehei, Kluyveromyces lactis, Pichia pastoris, Saccharomyces cerevisiae, Escherichia coli, Bacillus sublilis* or *Bacillus licheniformis*) or plant species (e.g., canola, soybean, corn, potato, barley, rye, wheat) may be used as host cells for the recombinant production of xylanase Cxy1. As the first step in the heterologous expression of xylanase Cxy1, an expression construct is assembled to include the cxy1 coding sequence and control sequences such as promoters, enhancers and terminators. Other sequences such as signal sequences and selectable markers may also be included. To achieve extracellular expression of xylanase Cxy1, the expression construct may include a secretory signal sequence. The signal sequence is not included on the expression construct if cytoplasmic expression is desired. The promoter and signal sequence are functional in the host cell and provide for expression and secretion of the Cxy1 protein. Transcriptional terminators are included to ensure efficient transcription. Ancillary sequences enhancing expression or protein purification may also be included in the expression construct.

Various promoters (transcriptional initiation regulatory region) may be used according to the invention. The selection of the appropriate promoter is dependent upon the proposed expression host. The promoter may be the native promoter associated with the cxy1 gene in the original *C. minitans* source. Alternatively, promoters from heterologous sources may be used as long as they are functional in the chosen host. Examples of heterologous promoters are the *E. coli* tac and trc promoters (Brosius et al., 1985), *Bacillus subtilis* sacB promoter and signal sequence (Wong, 1989), aox1 and aox2 from *Pichia pastoris* (Ellis et al., 1985), and oleosin seed specific promoter from *Brassica napus* or *Arabidopsis thaliana* (van Hartingsveldt et al., 1994).

Promoter selection is also dependent upon the desired efficiency and level of peptide or protein production. Inducible promoters such lac and aoxl are often employed in order to dramatically increase the level of protein expression. Overexpression of proteins may be harmful to the host cells. Consequently, host cell growth may be limited. The use of inducible promoter systems allows the host cells to be cultivated to acceptable densities prior to induction of gene expression, thereby facilitating higher product yields. If the protein coding sequence is to be integrated through a gene replacement (omega insertion) event into a target locus, then promoter selection may also be influenced by the degree of homology to the target locus promoter.

Various signal sequences may be used according to the invention. A signal sequence which is homologous to the cxy1 coding sequence may be used. Alternatively, a signal sequence which has been selected or designed for improved secretion in the expression host may also be used. For example, suitable signal sequence/host cell pairs include the *B. subtilis* sacB signal sequence for secretion in *B. subtilis,* and the *Saccharomyces cerevisiae* α-mating factor or *P. pastoris* acid phosphatase phoI signal sequences for *P. pastoris* secretion. A signal sequence with a high degree of homology to the target locus may be required if the protein coding sequence is to be integrated through an omega insertion event. The signal sequence may be joined directly through the sequence encoding the signal peptidase cleavage site to the protein coding sequence, or through a short nucleotide bridge consisting of usually fewer than ten codons.

Elements for enhancing transcription and translation have been identified for eukaryotic protein expression systems. For example, positioning the cauliflower mosaic virus (CaMV) promoter 1000 bp on either side of a heterologous promoter may elevate transcriptional levels by 10- to 400-fold. The expression construct should also include the appropriate translational initiation sequences. Modification of the expression construct to include the Kozak consensus sequence for proper translational initiation may increase the level of translation by 10 fold.

Elements to enhance purification of the protein may also be included in the expression construct. For instance, the product of oleosin gene fusions is a hybrid protein containing the oleosin gene joined to the gene product of interest. The fusion protein retains the lipophilic properties of oleosins and is incorporated in the oil body membranes (van Hartingsveldt el al. 1994). Association with the oil bodies may be exploited to facilitate purification of the recombinant oleosin fusion proteins (van Hartingsveldt et al., 1994). Vectors containing a polyhistidine tag can be used. The polyhistidine tag facilitates purification of the expressed polypeptide as it will bind to divalent cations such as $Ni^{2+}$ using known metal affinity chromatography protocols.

A selection marker is usually employed, which may be part of the expression construct or separate from it (e.g., carried by the expression vector), so that the marker may integrate at a site different from the gene of interest. Examples of these are markers that confer resistance to antibiotics (e.g., bla confers resistance to ampicillin for *E. coli* host cells, npII confers kanamycin resistance to *B. napus* cells) or that permit the host to grow on minimal medium (e.g., HIS4 enables *P. pastoris* GS 115 His to grow in the absence of histidine). The selectable marker will have its own transcriptional and translational initiation and termination regulatory regions to allow for independent expression of the marker. If antibiotic resistance is employed as a marker, the concentration of the antibiotic for selection will vary depending upon the antibiotic, generally ranging from 10 to 600 μg of the antibiotic/mL of medium.

The expression construct is assembled by employing known recombinant DNA techniques (Sambrook et al., 1989; Ausubel et al., 1999). Restriction enzyme digestion and ligation are the basic steps employed to join two fragments of DNA. The ends of the DNA fragment may require modification prior to ligation, and this may be accomplished by filling in overhangs, deleting terminal portions of the fragment(s) with nucleases (e.g., ExoIII), site directed mutagenesis, or by adding new base pairs by PCR. Polylinkers and adaptors may be employed to facilitate joining of selected fragments. The expression construct is typically assembled in stages employing rounds of restriction, ligation, and transformation of *E. coli.* Numerous cloning vectors suitable for construction of the expression construct are known in the art (λZAP and derived pBLUESCRIPT SK-1, Stratagene, 11011 North Torrey Pines Road, LaJolla, Calif. 92037, USA; pET, Novagen Inc. 597 Science Dr., Madison, Wis., 53711- cited in Ausubel et al., 1999) and the particular choice is not critical to the invention. The selection of cloning vector will be influenced by the gene transfer system selected for introduction of the expression construct into the host cell. At the end of each stage, the resulting construct may be analyzed by restriction, DNA sequence, hybridization and PCR analyses.

The expression construct may be transformed into the host as the cloning vector construct, either linear or circular, or may be removed from the cloning vector and used as-is or introduced onto a delivery vector. The delivery vector facilitates the introduction and maintenance of the expression construct in the selected host cell type. The expression construct is introduced into the host cells by any of a number of known gene transfer systems (e.g., natural competence, chemically mediated transformation, protoplast transformation, electroporation, biolistic transformation, transfection, or conjugation) (Ausubel et al., 1999; Sambrook et al., 1989). The gene transfer system selected depends upon the host cells and vector systems used.

For instance, the expression construct can be introduced into *Pichea pastoris* cells by protoplast transformation or electroporation. Electroporation of *P. pastoris* is readily accomplished, and yields transformation efficiencies comparable to spheroplast transformation. In this method, *P. pastoris* cells are washed with sterile water and resuspended in a low conductivity solution (e.g., 1 M sorbitol solution). A high voltage shock applied to the cell suspension creates transient pores in the cell membrane through which the transforming DNA (e.g., expression construct) enters the cells. The expression construct is stably maintained by integration, through homologous recombination, into the aox1 (alcohol oxidase) locus.

Alternatively, an expression construct, comprising the sacB promoter and signal sequence operably linked to the protein coding sequence, is carried on pUB110, a plasmid capable of autonomously replicating in *B. subtilis* cells. The resulting plasmid construct is introduced into *B. subtilis* cells by transformation. *Bacillus subtilis* cells develop natural competence (i.e. capability to take up and integrate foreign DNA) when grown under nutrient-poor conditions.

In a further alternative, relating to higher plants, *Brassica napus* cells are transformed by Agrobacterium-mediated transformation. The expression construct is inserted onto a binary vector capable of replication in *Agrobacterium tumefaciens* and mobilization into plant cells. The resulting construct is transformed into *A. tumefaciens* cells carrying an attenuated Ti or "helper plasmid". When leaf disks are infected with the recombinant *A. tumefaciens* cells, the expression construct is transferred into *B. napus* leaf cells by conjugal mobilization of the binary vector::expression construct. The expression construct integrates at random into the plant cell genome.

Host cells carrying the expression construct (i.e., transformed cells) are identified through the use of the selectable marker carried by the expression construct or vector, and the presence of the gene of interest confirmed by a variety of techniques including nucleic acid hybridization, PCR, and antibodies. After selection and screening, transformed plant cells can be regenerated into whole plants and varietal lines of transgenic plants developed and cultivated using known methods.

Transformed microbial cells may be grown by a variety of known techniques including batch and continuous fermentation on liquid or semi-solid media (Gerhardt el al., 1994). Transformed cells are propagated under conditions optimized for maximal product-to-cost ratios. Product yields may be dramatically increased by manipulation of cultivation parameters such as temperature, pH, aeration, and media composition. Careful manipulation and monitoring of the growth conditions for recombinant hyper-expressing *E. coli* cells may result in culture biomass and protein yields of 150 g (wet weight) of cells/L and 5 g of insoluble protein/L, respectively. Low concentrations of a protease inhibitor (e.g., phenylmethylsulfonyl fluoride or pepstatin) may be employed to reduce proteolysis of the over-expressed peptide or protein. Alternatively, protease deficient host cells may be employed to reduce or eliminate degradation of the desired protein.

Following fermentation, the microbial cells may be removed from the medium through known down-stream processes such as centrifugation and filtration. If the desired product is secreted, it can be extracted from the nutrient medium. In the case of intracellular production, the cells are harvested and the product released by rupturing cells through the application of mechanical forces, ultrasound, enzymes, chemicals and/or high pressure. Production of an insoluble product, such as occurs in hyper-expressing *E. coli* systems, can be used to facilitate product purification. The product inclusions can be extracted from disrupted cells by centrifugation, and contaminating proteins may be removed by washing with a buffer containing low concentrations of a denaturant (e.g., 0.5 to 6 M urea, 0.1 to 1% sodium dodecyl sulfate or 0.5 to 4.0 M guanidine-HCl). The washed inclusions may be solubilized in solutions containing 6 to 8 M urea, 1 to 2% sodium dodecyl sulfate or 4 to 6 M guanidine-HCl. Solubilized product can be renatured by slowly removing denaturing agents during dialysis.

If necessary, various methods for purifying the product from microbial fermentation may be employed. These include precipitation (e.g., ammonium sulfate precipitation), chromatography (gel filtration, ion exchange, affinity liquid chromatography), ultrafiltration, electrophoresis, solvent-solvent extraction (e.g., acetone precipitation), combinations thereof, or the like.

It will be apparent to those of ordinary skill in the art that alternative methods, reagents, procedures and techniques other than those specifically detailed herein can be employed or readily adapted to practice this invention. The invention is further illustrated in the following non-limiting Examples. All abbreviations used herein are standard abbreviations used in the art. Specific procedures not described in detail in the Examples are well-known in the art.

EXAMPLE 1

Cloning and Characterizing a Genomic Xylanase DNA Fragment from *Coniothyrium minitans*

Genomic DNA Isolation from *Coniothyrium Minitans* Strain LRS 2134

A wild type *Coniothyrium minitans* strain (*C. minitans* strain LRS 2134 - Lethbridge Research Centre Culture Collection, Agriculture and Agri-Food Canada, Lethbridge Research Centre, Lethbridge, Alberta, Canada), described in published International application No. PCT/CA98/00668, was inoculated into liquid potato dextrose broth (PDB) using mycelial plugs from *C. minitans* grown on potato dextrose agar (PDA). Cultures were grown with constant agitation (250 rpm) at 20° C. for 14 days. Cultures were harvested after two weeks by filtration using MIRACLOTH filtration cloth (Calbiochem, PO Box 12087, La Jolla, Calif. 92039-2087, USA, product #475855) and flash frozen in liquid nitrogen. Approximately 3 grams of frozen *C. minitans* mycelia was homogenized and thoroughly mixed with 20 ml of extraction buffer [100 mM Tris-HCl (pH 8.5), 100 mM NaCl, 50 mM ethylenediaminetetraacetic acid (EDTA) (pH 8.0), 2% sodium dodecyl sulfate (SDS; w/v), and 0.05 mg/ml proteinase K]. The mixture was incubated at 37° C. for one hour with tube inversion at regular intervals. The mixture was extracted once with 10 ml each of phenol and chloroform and precipitated with 0.6 volume of isopropanol. The genomic DNA was suspended in 0.5 ml of ultrapure water (OPTIMA, Fischer Scientific Ltd, 112 Colonnade Road, Nepean, Ontario K2E 7L6, product #W7-4) and stored at −20° C. for use as PCR template.

Primer Design for Polymerase Chain Reaction (PCR) Amplification of a Genomic *C. Minitans* Xylanase Fragment Xylanase amino-acid sequences from fungal species *Fursarium oxysporum* (Sheppard et al, 1994), *Aspergillus aculeatus* (Arai et al., 1998), Emericella nidulans (MacCabe et al., 1996), and *Humicola grisea* (likura et al., 1997) were aligned to search regions of homology. These four fungi represent divergent species. Two regions exhibiting homology were identified. Rather than utilizing the amino acid sequence to then deduce the DNA homology, the DNA sequences corresponding to these two regions of homology were directly compared to generate semi-degenerate primers Ff1 (5' gagaa(tc)agcatgaa(ag)tggga(tc)gc 3') SEQ ID NO: 3 and Fr5 (5' gtc(ag)g(act)(gac)ac(ta)ccccagac(ga)gt 3') SEQ ID NO: 5 in order to amplify a homologous xylanase fragment from *C. minitans* genomic DNA by PCR (FIG. 1). The DNA sequence represented by the Ff1 and Fr5 primer pair appeared to demonstrate a high-level of conservation at the nucleotide level with nucleotide ambiguities (at the third nucleotide) of either AG or TC pairs (which are common ambiguities generated by transition mutations during evolution). A/T and G/T substitutions were also observed for Fr5 while some substitutions were ignored in designing primers. In this manner, the Ff1/Fr5 primer pair was designed with high specificity to the target *C. minitans* xylanase sequence without high ambiguity.

PCR Amplification, Cloning and Sequencing of the Genomic *C. Minitans* Xylanase-like Fragment, Ffaml The PCR reactions consisted of 25 $\mu$l reactions containing 10 mM Tris-HCl (pH 8.0), 50 mM KCl, 1.5 mM $Mg^{2+}$, 0.8 mM each of primer Ff1 and Fr5, 1 U TAQ DNA POLYMERASE (Life Technologies, 8400 Helgerman Court, PO Box 6009, Gaithersburg, Md., 20898-9980, USA, product #10342-020) and 0.2 mM dNTP (each of dATP, dTTP, dGTP, and dCTP, Life Technologies, product #10297-018) mix. The PCR cycle profile consisted of progressive touch-down annealing steps in which the annealing temperature decreased progressively with each cycle. After an initial denaturing step of 1.5 minutes at 94° C., the cycle consisted of: (1) a denaturing step of 1.5 minutes at 94° C.; (2) an annealing step of one minute at 60° C.; and, (3) an extension step at 72° C. for two minutes. This cycle was repeated twenty times, the annealing temperature decreasing by 0.5° C. in each cycle, to a final annealing temperature of 50° C. This was followed by the same 3-step profile, annealing at 50° C., for an additional twenty cycles.

PCR reactions were resolved on a 1.5% agarose gel and visualized under UV light. PCR reactions were semi-purified by passage through a 1 ml SEPHADEX G-50 DNA grade M (Pharmacia, product no. 170045-01) column and ligated overnight into the pGEM-'T PCR vector system (Promega Corporation, 2800 Wood Hollow Road, Madison, Wis., 53711-5399, USA, product #A3600). The ligation mix was transformed into MAX EFFICIENCY DH5$\alpha$COMPETENT CELLS (Life Technologies, product #18258-012) and recombinant vectors were screened by blue-white/ampicillin selection (white $LacZ^-$ cells are indicative of recombinant clones, transformants are selected through ampicillin resistance). Plasmid DNA (pDNA) from recombinant clones was purified using the WIZARD PLUS miniprep purification system (Promega Corporation, product #A7500) and sequenced using the universal 24 base M13 forward (5' cgc cag ggt ttt ccc agt cac gac 3') and the 24 base reverse (5' agc gga taa caa ttt cac aca 3') sequencing primers using a fluorescent dye-terminator sequencing kit (ABI-PRISM BIGDYE TERMINATOR CYCLE SEQUENCING READY REACTION KIT, PE Applied Biosystems, 850 Lincoln Centre Drive, Foster City Calif., 94404, USA, product #4303149).

Characterizing the *C. Minitans* Xylanase-like Genomic Fragment Sequence

The sequence of the *C. minitans* 693 bp genomic fragment was obtained from the sequenced pGEM-T clone and entered into an alignment search algorithm (BLAST, Altschul et al., 1997) to identify homologous sequences. The *C. minitans* genomic fragment obtained by PCR demonstrated high homology to F-family fungal xylanases originating from *A. aculearus, E. nidulans, F. oxysporum* and *H. grisea* (Arai et al., 1998; Iikura et al., 1997; MacCabe et al., 1996; Ruiz-Roldan et al., 1998; Sheppard et al., 1994).

EXAMPLE 2

Assessing Presence, Size and Abundance of a *C. Minitans* Xylanase-like Hybridizing Transcript RNA Isolation from *C. Minitans* strains M11-3B 2A2, 2134 and A10-4

*C. minitans* strains M 11 -3B 2A2, 2134 and A 10-4 (Lethbridge Research Centre Culture Collection, Agriculture and Agri-Food Canada, Lethbridge Research Centre, Lethbridge, Alberta, Canada) were inoculated into minimal Czepek-Dox broth media (0.2% $NH_4H_2PO_4$, 0.1% $K_2HPO_4$, 0.05% $MgSO_4.7H_20$, 0.05% KCl, 0.001% $FeSO_4$, 0.00001% $ZnSO_4$, and 0.000005% $CuSO_4$; (all w/v)) supplemented with 1% ground sclerotia from *Sclerotinia sclerotiorum* as the sole carbon source, and PDB (potato dextrose broth). Cultures were incubated with constant agitation (250 rpm) at 20° C. for 14 days, and harvested by filtration with MIRACLOTH filtration cloth (Calbiochem). *C. minitans* tissue was flash frozen in liquid nitrogen and ground into a fine powder. Total RNA was extracted from ground *C. minitans* tissue using TRIZOL reagent (Life Technologies, product #15596-018).

Northern Hybridization Analysis of Total *C. Minitans* RNA

Ten micrograms of total RNA was loaded and resolved on a 1.5% agarose gel containing 1.9% formaldehyde, and 0.02M MOPS (3-(N-morpholino)propane sulfonic acid) buffer. The RNA was transferred to a nylon membrane (MAXIMUM STRENGTH NYTRAN, Schleicher & Schuell, PO Box 2012, Keene, N.H., 03431, USA, product #77404) by Northern transfer (Sambrook et al., 1989) and immobilized to it by UV crosslinking.

Nested primers were designed to amplify a subfragment from the *C. minitans* xylanase-like genomic fragment for constructing a radiolabeled probe for hybridization to total *C. minitans* RNA. Primers Ff1b (5' gacgtggaacattcaacttc 3') SEQ ID NO: 6 and Fr5b (5' ttcatgacggtgaggtagtc 3') SEQ ID NO: 7 were used to PCR-amplify a 604 bp xylanase-like subfragment which was subsequently [$^{32}$P]-$\alpha$CTP labeled by secondary PCR amplification. The radiolabeled xylanase subfragment was hybridized to total *C. minitans* RNA under semi-stringent conditions [55° C. overnight in 20 ml of hybridization buffer (1% (w/v) sarkosyl, 1.0 M NaCl (w/v), and 50 mM Tris-HCl (pH 7.5)), 0.4 ml of 50×Denhardt's solution (50×=1% (w/v) FICOLL (Type 400, Pharmacia, Baie D'Urfe, Quebec, Canada, product no. 17-0400-01), 1% (w/v) polyvinylpyrrolidone, 1% (w/v) bovine serum albumin), 10% dextran sulfate, and 20 $\mu$g of denatured herring sperm DNA] and washed under stringent conditions [two washes of 0.1×SSPE (20×SSPE =3.0 M NaCl, 0.2 M $NaH_2PO_4.H_2O$, 20 mM EDTA, pH 7.4), 0.1% SDS at 55° C. for 20 minutes]. The membrane was exposed to FUJI medical x-ray film RX (8"×10") autoradiographic film (Innomed Christie Group Ltd., 18208 $102_{nd}$Avenue, Edmonton, Alberta, Canada T5S 1S7, product #03E050) for 12 hours at −80° C. before development.

The resulting autoradiogram indicated significant expression of a 1.3 kb transcript which hybridized to the *C. minitans* genomic xylanase subfragment, indicating abundant expression of a xylanase-like transcript by *C. minitans* strain M11-3B 2A2 in the presence of ground sclerotia of *S. sclerotiorum* as the sole carbohydrate source. This xylanase-like transcript was also present (but less abundant) in total RNA extracted from wild-type strain 2134 and absent (or nearly absent) in strain A10-4 when grown in minimal Czepek-Dox medium in the presence of ground sclerotia of *S. sclerotiorum.* No xylanase-like transcript was observed in *C. minitans* strains 2134 (wild-type) A10-4 or M11-3B 2A2 cultured in glucose-rich PDB media.

EXAMPLE 3

Constructing and Screening a *C. minitans* cDNA Library in the Isolation and Sequencing of the Full-length Xylanase Transcript (cxy1)

*C. minitans* strain M11-3B 2A2 was grown for 15 days in Czepek -Dox broth media containing 1% ground sclerotia of *S. sclerotiorum* as the sole carbohydrate source. Mycelia was collected as in Example 2, and ground in liquid nitrogen. Total RNA was extracted using TRIZOL solution (Life Technologies). Transcript RNA was purified from the total RNA mixture using a cellulose-bound oligo-dT purification system (MESSAGEMAKER mRNA isolation system, Life Technologies, product #10551-018). First strand cDNA was synthesized from the purified mRNA using SUPERSCRIPT II RNAse H reverse-transcriptase (Life Technologies, product #18053-017) and was cloned unidirectionally into a λZAP-cDNA GIGAPACK III GOLD cloning kit (Stratagene product #200450). Bacteriophage clones were packaged using λphage GIGAPACK III GOLD packaging extract (Stratagene, product # 200450) and titered onto NZY agar media (1% (w/v) NZ amine, 0.5% (w/v) NaCl, 0.5% (w/v) yeast extract (Bacto), 0.2% (w/v) $MgSO_4.7H_2O$, pH 7.0). Phages were plated at a density of 50,000 per plate on 15 cm Petri plates.

Nested primers Ff1b and Fr5b were used to amplify and [$^{32}$P]-αCTP radiolabel the xylanase-like (F-family) fragment by PCR from *C. minitans* genomic DNA. The radiolabeled xylanase-like fragment was used to hybridize to plaque lifts from the cDNA library at 55° C. overnight in 20 ml hybridization buffer (see Example 2) (Sambrook el al., 1989). Positive xylanase-hybridizing clones underwent secondary and tertiary screens. Positive tertiary clones were excised into the pBLUESCRIPT plasmid using the EXASSIST system from the cloning kit (Stratagene, product #200450). A total of 100,000 recombinant clones were screened and two positive clones were identified in which one was a full-length cxy1 xylanase clone of 1269 bp with an open reading frame of 1155 bp (FIGS. 2A, 2B; SEQ ID NOS: 1 and 2). Both strands of the excised pBluescript clone were sequenced by primer walking using the ABI-PRISM BIGDYE TERMINATOR CYCLE SEQUENCING READY REACTION KIT, (PE Applied Biosystems, product #4303149). Sequences from both cDNA strands were found to be identical.

EXAMPLE 4

Characterization and Structural Analysis of cxy1 cDNA by Amino Acid Sequence Alignment Although fungal species may be phylogenetically disparate with regard to their non-functional genomic sequences, functional sequences required for specific biological function (such as catalytic and functional domains of cellulolytic enzymes) often show high levels of conservation. Thus, functional domains within Cxy1 may be identified through amino-acid sequence comparison with related fungal xylanases.

Cxy1 appears to share a standard structural layout with many other typical F-family fungal xylanases. Typical fungal xylanases such as the *Aspergillus kawachii* xylanase XynA (Ito el al., 1992) and the *Emericella nidulans* xylanase XylnC (MacCabe et al., 1996) consist of a unique N-terminus followed by a C-terminus catalytic domain. Although Cxy1 appears to share extensive homology throughout the C-terminus catalytic domain, the Cxy1 xylanase appears to include a carbohydrate-binding domain (CBD) (SEQ ID NO: 2 from amino acid 22 through amino acid 52) flanked by WSQCGG (SEQ ID NO: 2, amino acids 22–27) and WYFQC (SEQ ID NO: 2, amino acids 48–52) motifs. These are very similar to the signature WGQCGG and YYSQC sequences (Gilkes et al., 1991) reported for microbial glycanases, and the conservation of the overall sequence suggests that the sequence may retain carbohydrate-binding function. In cellulolytic or hemicellulolytic enzymes, the CBD domain functions to tether the enzyme to a cellulose or hemicellulose substrate, thus enhancing substrate specificity and degradative activity. The presence of a CBD-like sequence, however, does not in itself imply that an enzyme will demonstrate cellulolytic activity. For instance, the *Pseudomonas fluorescens* xylanase Xyna contains a cellulose-binding domain, but does not demonstrate hydrolytic activity towards carboxymethylcellulose (CMC)(Gilbert et al., 1988; Hall et al., 1989). Some xylanases exhibit dual cellulolytic and xylanolytic function. For example, the *Clostridium thermocellurn* F-family xylanase XynZ exhibits xylanase activity with high specificity and a small degree of cellulase activity (Greprinet et al., 1988).

The Cxy1 CBD is linked to the C-terminus catalytic domain by a unique linker sequence or hinge region (SEQ ID NO:2, amino acid 53 through amino acid 83) which may have function in coordinating the tertiary structure of the CBD and the catalytic domain during xylan catalysis (FIGS. 2A, 2B). This structural layout is similar to that of the F-family xylanase homologues Ffam1 and Xyl3 found in the fungal phytopathogen *Fursarium oxysporum* (Sheppard et al., 1994; Ruiz-Roldan et al., 1998). The Cxy1 xylanase exhibits high homology to all members of the F-family xylanases; regions of homology are most prominent at the catalytic C-terminal domain (FIGS. 3A, 3B). Sequence conservation is not limited to fungal F-family cellulases, but extends to prokaryotic F-family xylanases such as the thermostable xylanase XylA from the eubacteria *Thermomonospora alba* (Blanco et al., 1997), and the *C. thermocellum* XynY (Fontes et al, 1995).

EXAMPLE 5

Assaying Cxy1 xylanase activity in *Escherichia coli*

Many eukaryotic enzymes require extensive post-translational modification in order to retain their functional properties. Post-translational processing mechanisms such as glycosylation (addition of glycosyl groups to thr/ser (O-linked) or asn (N-linked) residues) and proteolytic cleavage often hinder functional reconstitution of eukaryotic proteins in prokaryotic systems. In contrast, a cxy1 cDNA llacZ fusion was found to produce a functional xylanase of significant levels in *Escherichia coli*. This implies that post-translational modification is not prerequisite for Cxy1 activity, and further suggests that Cxy1 is compatible with prokaryotic expression systems.

Sequence Verification of the lacZ/cxy1 Fusion Clone

Several pBLUESCRIPT clones containing the cxy1 insert were obtained by excision of the phagemid from the lambda vector originating from the *C. minitans* M11-3B 2A2 cDNA library. Excised pBLUESCRIPT-cxy1 clones were sequenced to determine whether the cxy1 insert would be transcribed into a translated Cxy1 fusion product with the upstream LacZ translational start sequence.

Assaying Xylanolytic Activity of the Cxy1/LacZ Fusion Protein from *E. Coli* (strain DH5α)

Recombinant fusion proteins in bacterial systems are usually sequestered within the cytoplasm in inclusion bodies. To measure cell-associated xylanase activity of the recombinant Cxy1 /LacZ fusion product from the *E. coli* clones, clones containing the cxy1 gene were grown 3 h in 2 ×YT broth [ 1.6% tryptone (Bacto), 1.0% yeast extract (Bacto), 1.0% NaCl, pH 7.0] in presence of ampicillin (100 µg/ml) with constant agitation. The inducer IPTG (isopropyl-β-D-thiogalactoside) was then added to a concentration of 0.5 mM, and cells were incubated overnight. Cells were pelleted (10,000x g for 1 min) in a 1.5 ml microtube, resuspended in 500 µl of 50 mM sodium phosphate buffer (pH 6.5) and washed twice before being sonicated for 15 seconds in 200 µl of ice-cold 50 mM sodium phosphate buffer, pH 6.5, 100 mM NaCl, 1 mM EDTA, and 5% glycerol using a Branson Sonifier (model # 250) equipped with a micro-tip probe and output set at 3 and 50%.

An aliquot of the disrupted cell lysate was heat-killed by boiling for 30 minutes as a heat-killed enzyme control. Non-recombinant pBLUESCRIPT clones (expressing the LacZ fragment only) were also included as a negative control. Twenty µl of non-heat-killed cell lysate and the heat killed control was spotted onto Luria-Bertani (LB) medium [1% (w/v) tryptone (Bacto), 0.5% (w/v) NaCl, 1% (w/v) yeast extract (Bacto), 1.5 % agarose, pH 7.0] containing either 0.1, 0.2 or 0.5% (w/v) of oat, birchwood, larchwood or RBB (4-o-methyl-Dβ-glucurono-D-xylan-Remazol Brilliant Blue R) xylan or carboxymethylcellulose (Sigma-Aldrich Canada Ltd. 2149 Winston Park Drive, Oakville, Ontario, Canada L6H 6J8, product # X-0627, X-0502, X-3875, M-5019 and C-5013 respectively) and incubated at 37° C. overnight. To visualize xylanolytic activity in the cell lysate, the plates were stained with 1.0% (w/v) congo red solution (except for RBB plates which are blue) for 30 minutes and de-stained with 1.0 M NaCl for 10 min (Wood et al., 1988). Secreted extracellular xylanase activity was also measured by spotting media from the cxy1 *E. coli* cultures onto xylan/agarose plates (incubated and stained as mentioned above). Xylanolytic activity was indicated by a clear region in a red stained background.

Xylanase activity was observed in the Cxy1/LacZ fusion protein where cell-lysate from *E. coli* cxy1/lacZ clones produced a zone of clearing on congo-red stained xylan/agarose plates (Table 1). This activity was ablated by extreme heat, indicated by the failure of heat-killed lysates to produce a clear zone on xylan/agarose plates. No clearing was produced by the supernatant fractions from cxy1/lacZ clones grown in LB (as well as the non-recombinant pBLUESCRIPT negative control), indicating the absence or insignificant presence of the Cxy1/LacZ fusion protein in the extracellular media.

Following sequencing, it was found that the construct was out of frame (frame 3) and that a stop codon had been introduced upstream of the cxy1 ATG codon. This may explain the leaky expression. To put the construct in frame, the plasmid was restricted with EcoRl (Life Technologies, product #15202-013), the ends polished with mung bean nuclease (Life Technologies, product #18041-012), the plasmid ligated with T4 DNA ligase (Life Technologies, product #15224-017) and transformed into MAX EFFICIENCY DH5α COMPETENT CELLS (Life Technologies, product #18258-012). More than 103 clones were tested by restriction analysis using EcoR1. More than half of the clones were not restricted by EcoR1. Seventeen of the non-restricted clones were sequenced. Eight clones had a deletion of three nucleotides, one clone had a deletion of five nucleotides, and the remaining eight had significant deletions. As an in-frame clone would have been expected to have a deletion of four nucleotides, it was apparent that a clone in the correct frame had not been obtained. In view of the significant deletions found, it is possible that an in-frame insertion of cxy1 in pBLUESCRIPT may have a deleterious effect in *E. coli*. Nevertheless, this experiment demonstrated that cxy1 is functional in a prokaryotic system.

EXAMPLE 6

Assaying Cxy1 xylanase activity in *Pichia pastoris*
Cloning and Expression of cxy1 in the Eukaryotic System of *Pichia Pastoris*

A cxy1 fragment was excised from the pBluescript/cxy1 clone by EcoRI/KpnI double digestion. The EcoRI/KpnI cxy1 fragment was unidirectionally subcloned into the pPICZαB expression vector (Invitrogen Corporation, 1600 Faraday Avenue, Carlsbad, Calif., 92008, USA) using EcoRI/Kpnl vector restriction sites. The 5' and 3' cloning junctions were sequenced to confirm that the subcloned fragment was in-frame. The resulting integration construct fused the cxy1 open-reading frame to the Pichia α-factor signal peptide (for secretion of the expressed Cxy1 product) under transcriptional regulation of a methanol-induced promoter. A linear integration construct was obtained after restriction with Pmel and electroporated into *P. pastoris* spheroplasts as recommended by the supplier of the vector. Integrants were selected on YPDS (Yeast Extract Peptone Dextrose Sorbitol; 1% yeast extract, 2% peptone, 2% dextrose, 1.0 M sorbitol, 2% agar) medium in presence of ZEOCIN (Invitrogen Corporation, product #R250-01) (100 µg/ml) and transferred on YPD (Yeast Extract Peptone Dextrose; 1% yeast extract, 2% peptone, 2% dextrose, 2% agar) medium in presence of ZEOCIN (Invitrogen Corporation) (100 µg/ml).

Positive integrants were grown 18 hours in methanol-free media, then cultures were diluted four-fold and cxy1 expression was induced by addition of 0.5% methanol. *P. pastoris* cultures were allowed to grow for an additional period of time ranging from one to six days. *P. pastoris* culture filtrates were collected by centrifugation for enzyme characterization.

Enzyme Assays and Cxy1 Characterization

*P. pastoris* cell lysate and culture filtrate were assayed for specific xylanolytic and glucanohydrolytic activity on birchwood, oat and xylan substrates in addition to carboxymethylcellulose (CMC), barley β-glucan, lichenan, and laminarin (at 1% (w/v) at a buffered pH of 6.8). The release of reducing ends by the xylanase activity was measured by colorimetric assay; 0.1 ml of cell lysate/culture filtrate was added to an equal volume of buffered substrate (1% oat spelt or birchwood xylan, laminarin, lichenan, barley β-glucan, CMC in 50 mM $NaPO_4$ buffer, pH 6.5) solution at 37° C. for 60 minutes. Reactions were terminated by a 0.3% (w/v) 3,6-dinitrophthalic acid in a 1.8 M $K_2CO_3$+0.1 M $Na_2S_2O_3$ (1:1) solution and heated at 90° C. for 10 minutes for color development. Absorbance of reactions was read at 490 nm. pH and temperature optima were determined for recombinant *P. pastoris* dialyzed filtrates (MW cut off=12,000 Da) by reducing sugar assay on oat xylan.

Cxy1 Enzyme Characterization

No hydrolytic activity was measured in non-recombinant control *P. pastoris* culture filtrates on xylan. No hydrolytic activity was measured in cxy1 recombinant and non-recombinant *P. pastoris* culture filtrates on CMC, barley β-glucan, lichenan, or laminarin. Temperature and pH optima for *P. pastoris* culture filtrates were determined to be, respectively, 47° C., and 7.5–8.0 using phosphate and Tris buffers.

Proteins were resolved by SDS polyacrylamide electrophoresis (SDS-PAGE) (Leammli, 1970). The gel (10% separating, 4% stacking) was cast and run with a MINI-PROTEAN II system (Bio-RAd Laboratories Ltd., Hercules, Calif.). The medium of P. pastoris was concentrated 50×using MICROCON 30 micro-concentrators (Amicon Inc, Beverly, Mass., product #42409) as described by the manufacturer. Concentrated protein samples were solubilized at 72° C. for 10 minutes in sample buffer (62.5 mM Tris-HCl, pH 6.8, 2% (w/v) SDS, 0.72 M β-mercaptoethanol, 10% (v/v), glycerol and 0.05% (w/v) bromophenol blue). Electrophoresis was carried out a room temperature at 80 V for 2 hours. Following electrophoresis, proteins were visualized by staining with Coomassie brilliant blue.

The predicted size of the xylanase polypeptide is around 41,000 Da. The expected size of the polypeptide inserted in the secretion vector pPICZαB and expressed by P. pastoris is around 44,000 Da. On an SDS-gel, a polypeptide of about 44,000 Da stainable with Coomassie blue is excreted by P. pastoris in the growth medium.

Xylanase activity (zymogram) was detected by separating the non-concentrated protein as above with the exception that 0.5% water soluble xylan (oat spelts, Sigma #X-0627) was incorporated during the casting of the gels. Following electrophoresis, the gels were soaked in 1% TRITON X-100 (t-Octylphenoxypolyethoxyethanol) for 1 hour at room temperature (3 changes at 200 ml per wash) to remove SDS, 50 mM phosphate buffer (pH 6.5) for 1 hour at 4° C. to renature the enzyme, and 50 mM phosphate buffer (pH 6.5) for 16 hours at 37° C. for enzyme activity. The enzyme bands were visualized by staining the gel with 1% Congo red for 1 hour and washing with 1 M NaCl.

A zymogram from an SDS gel, preceded by protein renaturation in non-ionic detergent, revealed a polypeptide of about 44,000 Da having strong xylanase activity and showing unequivocally an active sequence originating from C. minitans.

Although transgenic expression of the Cxy1 enzyme in either E. coli or P. pastoris failed to yield cellulolytic activity, the conservation of the carbohydrate-binding domain and the integrity of this homologous domain during the course of evolution suggests that carbohydrate-binding function may be important in the xylanolytic function by cxy1. Furthermore, cxy1 is derived from a unique glycosyl hydrolase gene family (F-family/family 10) comprising exoglucanases, xylanases, and dual specificity (glucanolytic and xylanolytic) hydrolases (Henrissat et al., 1989; Henrissat and Bairoch, 1993). This implies the evolutionary divergence of F-family hydrolases from an ancestral F-family precursor to yield functional enzymes with glucanolytic, xylanolytic or dual specificity enzymes.

The expression of cxy1 in *C. minitans* demonstrates the significance of xylanolytic degradation in its metabolic activities. Although the direct participation of Cxy1 in mycoparasitic processes has yet to be determined, cxy1 xylanase sequence conservation and expression in *C. minitans* imply a possible role for cxy1 in natural mycoparasitic activities. Moreover, the functional flexibility of cxy1 in prokaryotic and eukaryotic expression systems demonstrates the compatibility of cxy1 in biotechnological applications which employ either prokaryotic or eukaryotic settings.

TABLE 1

Xylanase activity of the xylanase clone cxyl from *Coniothyrium minitans* on different sources of xylan and cellulose.

| Substrate | Diameter of metabolized zone (mm) |
|---|---|
| RBB-xylan (0.1%) | 5.0 |
| oat xylan (0.2%) | 0.5 |
| oat xylan (0.2% + IPTG*) | 1.0 |
| oat xylan (0.5%) | 1.0 |
| birchwood xylan (0.2%) | 1.0 |
| birchwood xylan (0.5%) | 1.0 |
| larchwood xylan (0.5%) | 3.0 |
| CMC (0.5% + IPTG) | 0 |

RBB-xylan, 4-o-methyl-D-glucurono-D-xylan-Remazol Brilliant Blue R
CMC, carboxymethylcellulose
*IPTG (isopropyl-β-D-thiogalactoside) was added at 0.5 mM to the plate.

REFERENCES

Altschul, S. F., Madden T. L., Schaffer, A. A., Zhang, J., Zhang, Z., Miller, W. and Lipman, D. J. (1997). Gapped BLAST and PSI-BLAST: a new generation of protein database search programs. Nucleic Acids Res. 25: 3389–3402.

Arai, M., Kawaguchi, T. and Sumitani, J. (1998). Xylanase gene from *Aspergillus aculeatus*. Genbank accession no. AB013110, direct submission.

Ausubel, F. M., Bent, R., Kingston, R. E., Moore, D. J., Smith, J. A., Silverman, J. G. and Struhl, K. (1999). Current Protocols in Molecular Biology. John Wiley & Sons, Inc., New York.

Blanco, J., Coque, J. J., Velasco, J. and Martin, J. F. (1997). Cloning, expression in *Streptomyces lividans* and biochemical characterization of a thermostable endo-beta-1, 4-xylanase of *Thermomonospora alba* ULJB1 with cellulose-binding ability. Appl. Microbiol. Biotechnol. 48: 208–217.

Bieley, P. (1985). Microbial xylanolytic systems. Trends Biotechnol. 3: 286–290.

Brosius, J., Erfle, M. and Storella, J. (1985). Spacing of the −10 and −35 regions in the tac promoter. J. Biol. Chem. 260:3539–3541.

Davies, G. and Henrissat, B. (1995). Structures and mechanisms of glycosyl hydrolases. Structure 3:853–859.

Ellis, S. B., Brust, P. F., Koutz, P. J., Waters, A. F., Harpold, M. M., and Gingeras, R. R. (1985). Isolation of alcohol oxidase and two other methanol regulated genes from the yeast, Pichia pastoris. Mol. Cell. Biol. 5:1111–1121.

Fontes, C. M. G. A., Hazlewood, G. P., Morag, E., Hall, J., Hirst, B. H., and Gilbert, H. J. (1995). Evidence for a general role for non-catalytic thermostabilizing domains in xylanases from thermophilic bacteria. Biochem. J. 307: 151–158.

Gerhardt, P., Murray, R. G. E., Wood, W. A. and Krieg, N. R. (1994). Methods for General and Molecular Bacteriology. American Society for Microbiology. Washington, D. C., USA.

Gilbert, J. J., Sullivan, D. A., Jenkins, G., Kellett, L. E., Minton, N. P., et al. (1988). Molecular cloning of multiple xylanase genes from *Pseudomonas fluorescens* subsp. cellulosa. J. Gen. Microbiol. 134: 3239–3247.

Gilkes, N. R., Henrissat, B., Kilburn, D. G., Miller, R. C. Jr., and Warren, R. A. J. (1991). Domains in microbial β-1, 4-glycanases: sequence conservation, function, and enzyme families. Microbiol. Rev. 55: 303–315.

Greprinet, O., Chebrou, M.-C., and Beguin, P. (1988). Purification of *Clostridium thermoceilum* xylanase Z expressed in *Escherichia coli* and identification of the corresponding product in the culture medium of *Clostridium thermocellum*. J. Bacteriol. 170: 4576–4581.

Haas, H., Friedlin, E., Stoffler, G. and Redl, B. (1993). Cloning and structural organization of a xylanase-encoding gene from *Penicillium chrysogenum*. Gene 126: 237–242.

Hall, J., Hazlewood, G. P., Huskisson, N. S., Durrant, A. J., and Gilbert, H. J. (1989). Homology of a xylanase and cellulase from *Pseudomonas fluorescens* subsp. cellulosa: internal signal sequence and unusual protein processing. Mol. Microbiol. 3: 1211–1217.

Henrissat, B., Clayssens, M., Tomme, P., Lemesle, L. and Mornon, J.-P. (1989). Cellulase families revealed by hydrophobic cluster analysis. Gene 81: 83–95.

Henrissat, B. and Bairoch, A. (1993). New families in the classification of glycosyl hydrolases based on amino acid sequence similarities. Biochem. J. 293: 781–788.

Huang, H. C. and Hoes, J. A. (1976). Penetration and infection of *Sclerotinia sclerotiorum* by *Coniothyrium minitans*. Can. J. Bot. 54: 406–410.

Huang, H. C. and Kokko, E. G. (1987). Ultrastructure of hyperparasistism of *Coniothyrium minitans* on scierotia of *Sclerotinia sclerotiorum*. Can. J. Bot. 65: 2483–2489.

Huang, H. C. and Kokko, E. G. (1988). Penetration of hyphae of *Sclerotinia sclerotiorum* by *Coniothyrium minitans* without the formation of appressoria. Phytopath. Zeit. 123: 133–139.

Ito, K., Ikemasu, T. and Ishikawa, T. (1992). Cloning and sequencing of the xynA gene encoding xylanase A of *Aspergillus kawachii*. Biosci. Biotechnol. Biochem. 56: 906–912.

Iikura, H., Takashima, S., Nakamura, A., Masaki, H. and Uozumi, T. (1997). Cloning of a gene encoding a putative xylanase with a cellulose-binding domain from *Humicola grisea*. Genbank accession no. AB001030, direct submission.

Jones, D., Gordon, A. H. and Bacon, J. S. D. (1974). Cooperative action by endo- and exo-β-(1→3)-glucanases from parasitic fungi in the degradation of cell wall glucans of *Sclerotinia sclerotiorum* (Lib. ) de Bary. Biochem. J. 140: 45–55.

Leammli, U. K. (1970). Cleavage of structural proteins during the assembly of the head of bacteriophage T4. Nature 227: 680–685.

MacCabe, A. P., Fernandex-Espinar, M. T., de Graaff, L. H., Visser, J. and Ramon, D. (1996). Identification, isolation and sequence of the *Aspergillus nidulans* xlnC gene encoding the 34-kDa xylanase. Gene 175: 29–33.

Nielsen, H., Engelbrecht, J. Brunak, S. and von Heijne, G. (1997). Identification of prokaryotic and eukaryotic signal peptides and prediction of their cleavage sites. Protein Engineering. 10: 1–6.

Ruiz-Roldan, M. C., Huertas-Gonzalez, M. D., DiPietro, A. and Roncero, M. I. G. (1998). Two xylanase genes of the vascular wilt pathogen *Fursarium oxysporum* f. sp. lycopersici differentially expressed during infection of tomato plants. Genbank accession number AF052582, direct submission.

Sambrook, J., Fritsch, E. F. and Maniatis, T. (1989). Molecular Cloning, A Laboratory Manual. Cold Spring Harbor Laboratory Press.

Sheppard, P. O., Grant, F. J., Oort, P. J., Sprecher, C. A., Foster, D. C., Hagen, F. S., Upshall, A., McKnight, G. L., and O'Hara, P. J. (1994). The use of conserved cellulase family-specific sequences to clone cellulase homologue cDNAs from *Fursarium oxysporum*. Gene 150: 163–167.

van Hartingsveldt W., van Zeij, C. M. J., Harteveld, M. G., Gouka, R. J., Suykerbuyk, M. E. G., Luiten, R. G. M., Van Paridon, Selten, G. C. M., Veenstra, A. E., van Rooijen, G. J. H. and Moloney, M. M. (1994). Plant seed oil-bodies as carriers for foreign proteins. Bio/Technology 13:72–77

Wood, P. J., Erfle, J. D., and Teather, R. M. (1988). Use of complex formation between congo red and polysaccharides in detection and assay of polysaccharide hydrolases. Methods Enzymol. 160: 59–74.

Wong, S.-L. (1989). Development of an inducible and enhancible expression and secretion system in *Bacillus subtilis*. Gene 83:215–223.

All publications mentioned in this specification are indicative of the level of skill in the art to which this invention pertains. All publications are herein incorporated by reference to the same extent as if each individual publication was specifically and individually indicated to be incorporated by reference.

Although the foregoing invention has been described in some detail by way of illustration and example, for purposes of clarity and understanding it will be understood that certain changes and modifications may be made without departing from the scope or spirit of the invention as defined by the following claims.

What is claimed is:

1. An isolated nucleic acid molecule encoding a polypeptide having xylanolytic activity, said encoded polypeptide comprising an amino acid sequence selected from the group consisting of:
   a) an amino acid sequence depicted in SEQ ID NO: 2 from amino acid 84 to amino acid 384 or a functionally equivalent amino acid sequence having at least 85% homology thereto;
   b) an amino acid sequence depicted in SEQ ID NO: 2 from amino acid 22 to amino acid 384 or a functionally equivalent amino acid sequence having at least 85% homology thereto; or,
   c) an amino acid sequence depicted in SEQ ID NO: 2 from amino acid 1 to amino acid 384 or a functionally equivalent amino acid sequence having at least 85% homology thereto.

2. A nucleic acid molecule according to claim 1, wherein said encoded polypeptide comprises the amino acid sequence depicted in SEQ ID NO: 2 from amino acid 84 to amino acid 384 or a functionally equivalent amino acid sequence having at least 85% homology thereto.

3. A nucleic acid molecule according to claim 2, wherein said encoded polypeptide comprises the amino acid sequence depicted in SEQ ID NO: 2 from amino acid 84 to amino acid 384.

4. A nucleic acid molecule according to claim 3, said nucleic acid molecule comprising the nucleotide sequence depicted in SEQ ID NO: 1 from nucleotide 274 to nucleotide 1176.

5. A nucleic acid molecule according to claim 1, wherein said encoded polypeptide comprises the amino acid sequence depicted in SEQ ID NO: 2 from amino acid 22 to amino acid 384 or a functionally equivalent amino acid sequence having at least 85% homology thereto.

6. A nucleic acid molecule according to claim 5, wherein said encoded polypeptide comprises the amino acid sequence depicted in SEQ ID NO: 2 from amino acid 22 to amino acid 384.

7. A nucleic acid molecule according to claim 6, said nucleic acid molecule comprising the nucleotide sequence depicted in SEQ ID NO: 1 from nucleotide 88 to nucleotide 1176.

8. A nucleic acid molecule according to claim 1, wherein said encoded polypeptide comprises the amino acid sequence depicted in SEQ ID NO: 2 from amino acid 1 to amino acid 384 or a functionally equivalent amino acid sequence having at least 85% homology thereto.

9. A nucleic acid molecule according to claim 8, wherein said encoded polypeptide comprises the amino acid sequence depicted in SEQ ID NO: 2 from amino acid 1 to amino acid 384.

10. A nucleic acid molecule according to claim 9, said nucleic acid molecule comprising the nucleotide sequence depicted in SEQ ID NO: 1 from nucleotide 25 to nucleotide 1176.

11. An isolated nucleic acid molecule encoding a fragment of a polypeptide having xylanolytic activity, said polypeptide comprising a carbohydrate-binding domain, a catalytic domain, and a linker region operably linking said carbohydrate-binding domain and said catalytic domain, said encoded fragment comprising said carbohydrate-binding domain and said linker region and comprising an amino acid sequence depicted in SEQ ID NO: 2 from amino acid 22 to amino acid 83, or a functionally equivalent amino acid sequence having at least 85% homology thereto.

12. A nucleic acid molecule according to claim 11, wherein said encoded fragment of a polypeptide having xylanolytic activity comprises the amino acid sequence depicted in SEQ ID NO: 2 from amino acid 22 to amino acid 83.

13. A nucleic acid molecule according to claim 12, said nucleic acid molecule comprising the nucleotide sequence depicted in SEQ ID NO: 1 from nucleotide 88 to nucleotide 273.

14. A nucleic acid construct comprising a nucleic acid molecule of claim 11 operably linked to a nucleic acid molecule that encodes a catalytic domain of a hemicellulose-degrading enzyme and that is heterologous to said nucleic acid molecule of claim 11.

15. A vector comprising a nucleic acid molecule according to claim 1.

16. A cell other than *Coniothyrium minitans*, comprising a nucleic acid molecule according to claim 1.

17. A cell according to claim 16, wherein said cell is *Pichia pastoris*.

18. A method for producing a polypeptide having xylanolytic activity, comprising the steps of:
   a) culturing a cell comprising a nucleic acid molecule according to claim 1 under conditions conducive to an expression of a polypeptide encoded by said nucleic acid molecule; and,
   b) recovering said encoded polypeptide from the culture.

19. The method according to claim 18 wherein said cell is other than *Coniothyrium minitans*.

20. The method according to claim 18 wherein said cell is *Pichia pastoris*.

* * * * *

UNITED STATES PATENT AND TRADEMARK OFFICE
CERTIFICATE OF CORRECTION

PATENT NO.   : 6,121,034
DATED        : September 19, 2000
INVENTOR(S)  : Laroche et al.

It is certified that error appears in the above-identified patent and that said Letters Patent is hereby corrected as shown below:

Column 1,
Line 28, delete "endoxylanlolytic" and replace with -- endoxylanolytic --.

Column 2,
Line 58, delete "pl" and replace with -- pI --.

Column 4,
Line 33, delete "arc" and replace with -- are --.

Column 6,
Line 31, delete "G - C" and replace with -- G + C --.

Column 7,
Line 28, delete "teriary" and replace with -- tertiary --.
Line 30, delete "xylan" and replace with -- xylanase --.

Column 8,
Line 35, delete "Pichea" and replace with -- Pichia --.

Column 9,
Line 24, delete "lac" and replace with -- tac --.

Column 10,
Line 63, delete "Pichea"and replace with -- Pichia --.

Column 12,
Line 32, after "LRS 2134" insert -- on deposit with American Type Culture Collection, Manassas, VA under Accession No. 74415 --;
Line 61, delete "likura" and replace with -- Iikura --.

Column 13,
Line 66, delete "likura" and insert -- Iikura --.

Column 15,
Line 17, delete "H" and replace with -- H$^-$ --.

UNITED STATES PATENT AND TRADEMARK OFFICE
CERTIFICATE OF CORRECTION

PATENT NO.     : 6,121,034
DATED          : September 19, 2000
INVENTOR(S)    : Laroche et al.

It is certified that error appears in the above-identified patent and that said Letters Patent is hereby corrected as shown below:

Column 16,
Line 20, delete "*thermocellurn*" and replace with -- thermocellum --
Line 51, delete "cxyl cDNA llacZ" and replace with -- cxyl cDNA/lacZ --.

Column 17,
Line 40, after "where" insert -- a --.

Column 18,
Line 24, delete "PmeI" and replace with -- PmeI --.

Column 20,
Line 67, delete "*thermoceilum*" and replace with -- *thermocellum* --.

Column 21,
Line 43, delete "Leammli" and replace with -- Laemmli --.

Signed and Sealed this

Twenty-ninth Day of July, 2003

JAMES E. ROGAN
*Director of the United States Patent and Trademark Office*